United States Patent
Leblanc et al.

(10) Patent No.: US 6,486,142 B2
(45) Date of Patent: Nov. 26, 2002

(54) PHOSPHONIC ACID DERIVATIVES AS INHIBITORS OF PROTEIN TYROSINE PHOSPHATASE 1B (PTP-1B)

(75) Inventors: Yves Leblanc, Kirkland (CA); Claude Dufresne, Dollard des Ormeaux (CA); Jacques Yves Gauthier, Laval (CA); Cheuk Kun Lau, Ile Bizard (CA); Chun Sing Li, Dollard des Ormeaux (CA); Patrick Roy, Dollard des Ormeaux (CA); Michel Therien, Laval (CA); John Scheigetz, Dollard des Ormeaux (CA); Zhaoyin Wang, Kirkland (CA)

(73) Assignee: Merck Frosst Canada & Co., Kirkland (CA)

( * ) Notice: Subject to any disclaimer, the term of this patent is extended or adjusted under 35 U.S.C. 154(b) by 0 days.

(21) Appl. No.: 09/745,211

(22) Filed: Dec. 21, 2000

(65) Prior Publication Data

US 2002/0058644 A1 May 16, 2002

Related U.S. Application Data

(60) Provisional application No. 60/171,520, filed on Dec. 22, 1999.

(51) Int. Cl.$^7$ .......................... C07F 9/38; A61K 31/663
(52) U.S. Cl. .......................... 514/80; 514/92; 514/125; 548/113; 548/119; 558/198; 562/23; 562/24; 562/25
(58) Field of Search ................... 548/119, 113; 562/23, 24, 25; 558/198; 514/80, 92, 125

(56) References Cited

U.S. PATENT DOCUMENTS 6,066,715 A    3/2000   Desmarais et al.

FOREIGN PATENT DOCUMENTS

| WO | WO97/40017 | 10/1997 |
| WO | WO 98/20156 | 5/1998 |
| WO | WO 99/31066 | 6/1999 |
| WO | WO 99/47529 | 9/1999 |
| WO | WO 00 17211 | 3/2000 |

OTHER PUBLICATIONS

Charifson, et al., Biochemistry, US, American Chemical Society, 1997, pp. 6283–6293, vol. 36–No. 21.
Desmarais, S., et al., Biochemical Journal, 1999, pp. 219–223, vol. 337–No.2.
Taing, M., Biochemistry, 1999, pp. 3793–3803, vol. 38–No. 12.
Ahmad, et al., J. Biol. Chem., vol. 270, pp. 20503–20508, 1995.
Bin, et al., Tetrahedron, vol. 52, No. 30, pp. 9963–9970.
Caplan, et al, Bioorganic & Medicinal Chem. Letters, vol. 8, No. 5, pp. 515–520.
Charbonneau, et al, Proc. Natl. Acad Sci. USA, vol. 86, pp. 5252–5256, 1989.
Fishcer, et al., Science, vol. 253, pp. 401–406, 1991.
Goldstein, Receptor vol. 3, pp. 1–15, 1993.
Kotoris, et al., J. Org. Chem., vol. 63, pp. 8052–8057, 1998.
Seely, et al., Diabetes, vol. 45, pp. 1379–1385, 1996.
Taylor, et al., Bioorg. Med. Chem., vol. 6(9), pp. 1457–1468, 1998.
Taylor, et al., Bioorg. Med. Chem., vol. 6, p. 2235, 1998.
Taylor, et al., Tetrahedron Letters, vol. 8, No. 45, pp. 8089–8092, 1996.
Taylor, et al., Tetrahedron, No. 54, pp. 1691–1714, 1998.
Wang, et al., Bioorg. Med. Chem., Let., vol. 8(4), pp. 345–350, 1998.
White, et al., J. Biol. Chem., vol. 269, pp. 1–4, 1994.
Yokomatsu, et al., Tetrahedron, vol. 54, No. 32, pp. 9341–9356.
Burke, et al., Bioorg. Med. Chem. Letters, vol. 9, pp. 347–352, 1999.
Yao, et al., Tetrahedron, vol. 55, pp. 2865–2874, 1999.
Beaulieu, et al.., J. Med. Chem., vol. 42, pp. 1757–1766, 1999.
Kotoris, et al., Bioorg. Med. Chem., vol. 8, pp. 3275–3280, 1998.

*Primary Examiner*—Robert Gerstl
(74) *Attorney, Agent, or Firm*—James L. McGinnis; Melvin Winokur

(57) ABSTRACT

The invention encompasses the novel class of compounds represented by formula I, which are inhibitors of the PTP-1B enzyme.

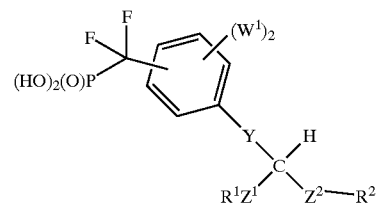

The invention also encompasses pharmaceutical compositions and methods of treating or preventing PTP-1B mediated diseases, including diabetes, obesity, and conditions related to diabetes.

29 Claims, No Drawings

PHOSPHONIC ACID DERIVATIVES AS INHIBITORS OF PROTEIN TYROSINE PHOSPHATASE 1B (PTP-1B)

CROSS REFERENCE TO RELATED APPLICATIONS

This application is based on and claims priority from U.S. Provisional Application No. 60/171,520, which was filed on Dec. 22, 1999, and which is incorporated by reference into this application. Commonly assigned U.S. application Ser. No. 09/398,356, filed on Sep. 17, 1999, now U.S. Pat. No. 6,174,874, and commonly assigned U.S. application Ser. Nos. 09/745,220, 09/745,199 and 09/745,222, all filed on even date herewith, contain related subject matter.

BACKGROUND OF THE INVENTION

This invention relates to a novel class of phosphonic acid derivatives that are inhibitors of PTP-1B.

Protein tyrosine phosphatases are a large family of transmembrane or intracellular enzymes that dephosphorylate substrates involved in a variety of regulatory processes (Fischer et al., 1991, Science 253:401–406). Protein tyrosine phosphatase-1B (PTP-1B) is a ~50 kd intracellular protein present in abundant amounts in various human tissues (Charbonneau et al., 1989, Proc. Natl. Acad. Sci. USA 86:5252–5256; Goldstein, 1993, Receptor 3:1–15).

Determining which proteins are substrates of PTP-1B has been of considerable interest. One substrate which has aroused especial interest is the insulin receptor. The binding of insulin to its receptor results in autophosphorylation of the receptor, most notably on tyrosines 1146, 1150, and 1151 in the kinase catalytic domain (White & Kahn, 1994, J. Biol. Chem. 269:1–4). This causes activation of the insulin receptor tyrosine kinase, which phosphorylates the various insulin receptor substrate (IRS) proteins that propagate the insulin signaling event further downstream to mediate insulin's various biological effects.

Seely et al., 1996, Diabetes 45:1379–1385 ("Seely") studied the relationship of PTP-1B and the insulin receptor in vitro. Seely constructed a glutathione S-transferase (GST) fusion protein of PTP-1B that had a point mutation in the PTP-1B catalytic domain. Although catalytically inactive, this fusion protein was able to bind to the insulin receptor, as demonstrated by its ability to precipitate the insulin receptor from purified receptor preparations and from whole cell lysates derived from cells expressing the insulin receptor.

Ahmad et al., 1995, J. Biol. Chem. 270:20503–20508 used osmotic loading to introduce PTP-1B neutralizing antibodies into rat KRC-7 hepatoma cells. The presence of the antibody in the cells resulted in an increase of 42% and 38%, respectively, in insulin stimulated DNA synthesis and phosphatidyinositol 3' kinase activity. Insulin receptor autophosphorylation and insulin receptor substrate-1 tyrosine phosphorylation were increased 2.2 and 2.0-fold, respectively, in the antibody-loaded cells. The antibody-loaded cells also showed a 57% increase in insulin stimulated insulin receptor kinase activity toward exogenous peptide substrates.

Recently, Kennedy et al., 1999, Science 283: 1544–1548 showed that protein tyrosine phosphatase PTP-1B is a negative regulator of the insulin signalling pathway, suggesting that inhibitors of this enzyme may be beneficial in the treatment of Type 2 diabetes. Mice lacking PTP-1B are resistant to both diabetes and obesity.

Thus, inhibitors of PTP-1B improve insulin-sensitivity. They have utility in controlling or treating Type 1 and Type 2 diabetes, in improving glucose tolerance, and in improving insulin sensitivity in patients in need thereof. The compounds may also be useful in treating or preventing cancer, neurodegenerative diseases and the like.

SUMMARY OF THE INVENTION

Compounds represented by Formula I, and pharmaceutically acceptable salts thereof, and prodrugs thereof, are PTP-1B inhibitors and are useful in the treatment of diabetes, obesity and related conditions.

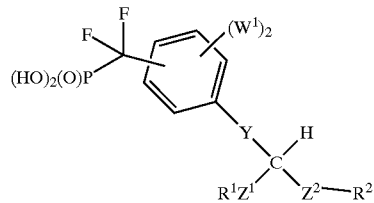

I

In the compounds having Formula I, $R^1$ and $R^2$ are selected from the group consisting of:
$C_{1-10}$alkyl$(R^a)_{0-7}$, $C_{2-10}$alkenyl$(R^a)_{0-7}$, Aryl$(R^a)_{0-3}$ and Het$(R^a)_{0-3}$;

wherein, each $R^a$ independently represents a member selected from the group consisting of: Aryl, OH, CN, halogen, $CO_2H$, $CO_2C_{1-6}$alkyl, $OC_{1-6}$alkyl, $C_{1-6}$alkyl, $OC_{1-10}$alkyleneCO$_2$H, O Aryl, $C_{0-6}$alkyleneSO$_3$H, $C_{0-6}$alkyleneCO$_2$H, $C_{0-6}$alkyleneCO$_2C_{1-6}$alkyl, $C_{0-6}$alkyleneCO$_2C_{2-6}$alkenyl, $C_{0-6}$alkyleneC(O)C$_{1-6}$alkyl, $C(O)NR_3 R_4$, $NR_3 R_4$, $C_{1-6}$haloalkyl, $OC_{1-6}$haloalkyl, $S(O)_yC_{1-6}$alkyl, $S(O)_yNR^{3'}R^{4'}$, and Het, wherein y is 0, 1, or 2, wherein Het, Aryl, alkyl, and alkenyl in $R^a$ are optionally substituted with 1–3 substituents independently selected from halogen, $C_{1-6}$alkyl, $C_{1-6}$haloalkyl, $CO_2H$, $CO_2C_{1-6}$alkyl, $OC_{1-10}$alkyl, OH, Het and Aryl, where said Het and Aryl are optionally substituted with 1–2 substituents independently selected from halogen, $C_{1-3}$alkyl, $OC_{1-3}$alkyl, $CF_3$, and $OCF_3$;

Aryl is a 6–14 membered carbocyclic aromatic ring system comprising 1–3 phenyl rings, wherein said rings are fused together so that adjacent rings share a common side when there is more than one aromatic ring;

Het represents a 5–10 membered aromatic ring system comprising one ring or two fused rings, 1–4 heteroatoms, 0–4 of which are N atoms and 0–2 of which are O or S(O)$_y$ wherein y is 0–2, and 0–2 carbonyl groups;

Y, $Z^1$ and $Z^2$ each independently represent —(CR$^3$R$^4$)$_a$—X—(CR$^3$R$^4$)$_b$— wherein a and b are either 0 or 1, such that the sum of a and b equals 0, 1 or 2;

X represents a bond, O, S(O)$_y$, NR$^{3'}$, C(O), OC(O), C(O)O, C(O)NR$^{3'}$, NR$^{3'}$C(O) or —CH═CH—, where y is as previously defined;

$R^3$ and $R^4$ are independently H, halo, $C_{1-3}$alkyl, or $C_{1-3}$haloalkyl;

each $R^{3'}$ is independently selected from the group consisting of: H, $C_{1-6}$alkyl, $C_{1-6}$haloalkyl, OH, C(O)C$_{1-6}$alkyl, C(O)Aryl, C(O)Het, C(O)C$_{1-6}$haloalkyl, Aryl and Het;

each $R^{4'}$ is independently selected from the group consisting of: H, $C_{1-6}$alkyl, $C_{1-6}$haloalkyl, Aryl and Het; and each $W^1$ is independently selected from the group consisting of: H, OH, CN, halogen, OC$_{1-6}$alkyl$(R^a)_{0-3}$, S(O)$_y$C$_{1-6}$alkyl$(R^a)_{0-3}$, with y equal to 0–2, S(O)$_3$H, $C_{1-6}$alkyl$(R^a)_{0-3}$, $C_{1-6}$haloalkyl$(R^a)_{0-3}$, $CO_2H$, $CO_2C_{1-6}$alkyl $(R^a)_{0-3}$, $CO_2C_{1-6}$haloalkyl$(R^a)_{0-3}$, $CO_2C_{2-6}$ alkenyl$(R^a)_{0-3}$, $C(O)C_{1-6}$alkyl$(R^a)_{0-3}$, $C(O)NR^{3'}R^{4'}$, $S(O)_y$ $NR^{3'}R^{4'}$, $NR^{3'}R^{4'}$, Aryl and Het, wherein $R^{3'}$ and $R^{4'}$ are as defined above, and wherein Aryl and Het may be unsubstituted or are optionally substituted with 1–3 substituents independently selected from the group consisting of halogen, $C_{1-6}$alkyl, $C_{1-6}$haloalkyl, $CO_2H$, $CO_2C_{1-6}$alkyl, $OC_{1-6}$alkyl, $OC_{1-6}$haloalkyl, and OH; or the two $W^1$ groups are on adjacent positions of the aromatic ring and are taken in combination to represent a fused phenyl ring.

Methods of treating, controlling and preventing diabetes, obesity, and other related diseases and conditions using the compounds of Formula I are taught herein. Pharmaceutical compositions and combination therapies are also disclosed herein.

DETAILED DESCRIPTION OF THE INVENTION

In a subset of compounds of Formula I, each $W^1$ represents H or halogen. In a preferred subset of these compounds, one $W^1$ group represents H and the other $W^1$ group represents a halogen in the position adjacent to $-CF_2P(O)(OH)_2$ on the aromatic ring.

In a subset of any of the groups of compounds above, each Het is selected from the group consisting of pyridinyl, 1H-1,2,3-benzotriazolyl, 1,2,4-oxadiazolyl and 1,3-thiazolyl.

In one embodiment of this invention, Y is $-CH_2-$.

In another embodiment of compounds in accordance with claim 1, $Z^1$ and $Z^2$ are each independently selected from the group consisting of $CH_2$, $-C(O)-$, and a direct bond.

Another embodiment comprises compounds in which $R^1$ and $R^2$ are each independently selected from the group consisting of Aryl$(R^a)_{0-3}$ and Het$(R^a)_{0-3}$.

In another embodiment, $R^1$ and $R^2$ of Formula I are each independently selected from the group consisting of
  (a) $(CH_2)_{0-3}$phenyl, which is optionally mono, di-, or trisubstituted, wherein the substituents are selected from the group consisting of:
    (1) halo,
    (2) $C_{1-6}$alkoxy,
    (3) $C_{1-6}$alkylthio,
    (4) $C_{1-6}$alkyl,
    (5) $C_{1-6}$fluoroalkyl,
    (6) $-CO_2H$,
    (7) $-CO_2-C_{1-4}$alkyl,
    (8) $-CO_2C_{1-4}$fluoroalkyl,
    (9) heteroaryl, which is optionally mono, di-, or trisubstituted, wherein the substituents are independently selected from the group consisting of halogen, $C_{1-6}$alkoxy, $C_{1-6}$alkylthio, $C_1-C_6$fluoroalkyl, $C_{1-6}$alkyl, $-CO_2H$, $-CO_2C_{1-4}$alkyl, $-CO_2C_{1-4}$fluoroalkyl, phenyl, and heteroaryl, wherein the phenyl and heteroaryl are optionally substituted with 1–2 groups independently selected from the groups listed in (a)(1)–(a)(8) of this paragraph, and
    (10) phenyl, which is optionally substituted with 1–2 substituents independently selected from the group consisting of halogen, $C_{1-6}$alkoxy, $C_{1-6}$alkylthio, $C_{1-6}$alkyl, $C_{1-6}$fluoroalkyl, $-CO_2H$, $-CO_2C_{1-4}$alkyl, $-CO_2C_{1-4}$fluoroalkyl, phenyl and heteroaryl, wherein the phenyl and heteroaryl are optionally substituted with 1–2 groups independently selected from the groups listed in (a)(1)–(a)(8) of this paragraph, and
  (b) heteroaryl, which is optionally mono-, di- or trisubstituted, wherein the substituents are independently selected from the group consisting of:
    (1) halo,
    (2) $C_{1-6}$alkoxy,
    (3) $C_{1-6}$alkylthio,
    (4) $C_{1-6}$fluoroalkyl,
    (5) $C_{1-6}$alkyl,
    (6) $-CO_2H$,
    (7) $-CO_2-C_{1-4}$alkyl,
    (8) $-CO_2C_{1-4}$fluoroalkyl,
    (9) phenyl, which is optionally substituted with 1–2 substituents independently selected from the group consisting of halogen, $C_{1-6}$alkoxy, $C_{1-6}$alkylthio, $C_{1-6}$alkyl, $C_{1-6}$fluoroalkyl, $CO_2H$, $-CO_2C_{1-4}$alkyl, $-CO_2C_{1-4}$fluoroalkyl, phenyl and heteroaryl, wherein the phenyl and heteroaryl are optionally substituted with 1–2 groups independently selected from the groups listed in (a)(1)–(a)(8) of this paragraph, and
    (10) heteroaryl, which is optionally substituted with 1–2 substituents independently selected from the group consisting of halogen, $C_{1-6}$alkoxy, $C_{1-6}$alkylthio, $C_{1-6}$-alkyl, $C_{1-6}$fluoroalkyl, phenyl and heteroaryl, wherein the phenyl and heteroaryl are optionally substituted with 1–2 groups independently selected from the groups listed in (a)(1)–(a)(8) of this paragraph,
  wherein each $W^1$ is independently selected from the group consisting of: halogen, $C_{1-6}$alkyl, and $C_{1-6}$fluoroalkyl;
  Y is $-CH_2-$; and
  $Z^1$, and $Z^2$ are independently selected from the group consisting of $CH_2$, $CH_2CH_2$, $C(O)$, $C(O)CH_2$, $CH_2C(O)-$, $-OC(O)-$, $C(O)O$, and a direct bond.

In another subset of compounds,
$R^1$ and $R^2$ are each independently selected from the group consisting of $-(CH_2)$phenyl, phenyl, 1,2,4-oxadiazolyl, pyridinyl, and 1H-1,2,3-benzotriazolyl, each of which is optionally substituted with 1–3 substituents independently selected from halogen, $C_{1-3}$alkyl, $CF_3$, phenyl and 1,2,4-oxadiazolyl, wherein phenyl and 1,2,4-oxadiazolyl are optionally substituted with 1–3 substituents independently selected from $C_{1-3}$alkyl, $CF_3$, phenyl, and 1,2,4-oxadiazolyl,
  $Z^1$ and $Z^2$ are each CO, $-OC(O)-$, $-C(O)O-$, or a direct bond,
  Y is $CH_2$, and
  each $W^1$ is independently selected from the group consisting of hydrogen, halogen, and $C_{1-3}$alkyl, and is in a position on the aromatic ring adjacent to the $-CF_2P(O)(OH)_2$ group.

Finally, specific embodiments of compounds of Formula I are provided in Table 1, Table 2, and/or the compounds exemplified in Examples 1–24, which are named below:

Example 1: [2-bromo-4-(3-oxo-2,3-diphenylpropyl)phenyl] (difluoro)methylphosphonic acid;

Example 2: Difluoro(4-(3-oxo-2,3-diphenylpropyl)phenyl] methylphosphonic acid;

Example 3: 4-[2-(Benzyloxy)-1-(methoxycarbonyl)-2-oxoethyl]phenyl(difluoro) methylphosphonic acid;

Example 4: 2-Bromo-4-[2-phenyl-2-(3-phenyl-1,2,4-oxadiazol-5-yl) ethyl]phenyl (difluoro)methylphosphonic acid;

Example 5: 2-Bromo-4-[2-phenyl-2-(5-phenyl- 1,2,4-oxadiazol-3-yl)ethyl]phenyl (difluoro)methylphosphonic acid;

Example 6: [4-(2-Benzotriazol-1-yl-2-m-tolylethyl)-phenyl] difluoromethylphosphonic acid;

Example 7: {4-[2-Benzotriazol-1-yl-2-(4-fluorophenyl)-ethyl]-2-bromophenyl }difluoromethyl phosphonic acid;

Example 8: {4-[2-Benzotriazol-1-yl-2-(4-trifluoromethylphenyl)-ethyl]phenyl}difluoromethylphosphonic acid disodium salt;

Example 9: (4-2-(1H-1,2,3-Benzotriazol-1-yl)-2-[4-(methyloxycarbonyl)phenyl]ethylphenyl)(difluoro)methylphosphonic acid;

Example 10: {4-[2-(1H-1,2,3-benzotriazol-1-yl)-2-(4-fluorophenyl)ethyl]phenyl } (difluoro)methylphosphonic acid;

Example 11: {4-[2-(1H-1,2,3-benzotriazol-1-yl)-2-phenylethyl]phenyl}(difluoro) methylphosphonic acid;

Example 12: {[(2,2-dimethylpropanoyl)oxy]methyl}hydrogen [2-bromo-4-(3-oxo-2,3-diphenylpropyl)phenyl](difluoro)methylphosphonate;

Example 13: Bis {[(2,2-dimethylpropanoyl)oxy]methyl}[2-bromo-4-(3-oxo-2,3-diphenylpropyl) phenyl](difluoro) methylphosphonate;

Example 14: 1-{[[[2-bromo-4-(3-oxo-2,3-diphenylpropyl)phenyl)(difluoro)methyl](hydroxy)phosphoryl]oxy}-2-methylpropyl propionate;

Example 15: [1-(isobutyryloxy)ethyl]hydrogen[2-bromo-4-(3-oxo-2,3-diphenylpropyl)phenyl](difluoro) methylphosphonate;

Example 16: Bis[(isobutyryloxy)methyl][2-bromo-4-(3-oxo-2,3-diphenylpropyl)phenyl](difluoro) methylphosphonate;

Example 17: [(isobutyryloxy)methyl]hydrogen [2-bromo-4-(3-oxo-2,3-diphenylpropyl)phenyl](difluoro) methylphosphonate;

Example 18: Bis{[(isopropoxycarbonyl)oxy]methyl}[2-bromo-4-(3-oxo-2,3-diphenylpropyl) phenyl](difluoro) methylphosphonate;

Example 19: [(isopropoxycarbonyl)oxy]methyl hydrogen [2-bromo-4-(3-oxo-2,3-diphenyl)phenyl](difluoro) methylphosphate;

Example 20: Dibenzyl[2-bromo-4-(3-oxo-2,3-diphenylpropyl)phenyl](difluoro)methylphosphonate;

Example 21: Benzyl hydrogen [2-bromo-4-(3-oxo-2,3-diphenylpropyl)phenyl](difluoro) methylphosphonate;

Example 22: [2-bromo-4-(3-oxo-2-phenylbutyl)phenyl] (difluoro)methylphosphonic acid;

Example 23: {2-bromo-4-[3-oxo-2-phenyl-3-(1,3-thiazol-2-yl)propyl]phenyl}(difluoro) methylphosphonic acid; and Example 24: {2-bromo-4-[2-(4-methoxy-1,3-thiazol-2-yl)-3-oxo-3-phenylpropyl)phenyl}(difluoro) methylphosphonic acid.

Methods of treating, preventing, or controlling diabetes and other diseases using the compounds of Formula I are disclosed herein. A method of treating, controlling or preventing diabetes and complications thereof in a mammalian patient in need of such treatment includes the administration to the patient an anti-diabetic effective amount of a compound of Formula I. A method of treating, controlling or preventing obesity in a mammalian patient in need of such treatment comprises the administration to the patient of an anti-obesity effective amount of a compound in accordance with claim 1. Such methods also include the administration of a second compound, which may be an anti-diabetic compound, an anti-obesity compound, or an HMG-CoA reductase inhibitor, in an amount effective to treat, control or prevent diabetes or obesity, or to improve a poor lipid profile.

A method of treating, controlling or preventing atherosclerosis in a mammalian patient in need of such treatment comprises administering to the patient an effective amount of a compound of Formula I and an effective amount of an HMG-CoA reductase inhibitor.

More generally, compounds of Formula I may be used as the active compound in a method for treating, preventing, or controlling one or more diseases or conditions selected from Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease. The method comprises the administration of an effective amount of the compound of Formula I. Combination treatments can also be used in which case, the method comprises the administration of a compound of Formula I and an effective amount of one or more pharmaceutically active compounds selected from the group consisting of an HMG-CoA reductase inhibitor, an anti-obesity agent, and an antidiabetic compound.

Pharmaceutical compositions also can be made using the compounds of Formula I. Compositions that are suitable for the treatment, prevention or control of one or more diseases or conditions selected from Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease contain an effective amount of a compound of Formula I in combination with a pharmaceutically acceptable carrier.

Such pharmaceutical compositions may also include a second anti-diabetic agent or an anti-obesity agent. They may also include a cholesterol lowering agent. Pharmaceutical compositions may therefore include: (1) an effective amount of a compound of Formula I, (2) an effective amount of one or more pharmaceutically active compounds selected from the group consisting of an HMG-CoA reductase inhibitor, an anti-obesity agent, and an anti-diabetic agent, and (3) a pharmaceutically acceptable carrier.

Such pharmaceutical compositions that contain a second active compound or composition and that are suitable for the treatment, prevention or control of one or more diseases or conditions selected from the group consisting of Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease, may be comprised of the following:

(1) an effective amount of a compound of Formula 1;
(2) an effective amount of one or more pharmaceutically active compounds listed below; and
(3) a pharmaceutically acceptable carrier; where the pharmaceutically active compounds are selected from the group consisting of:
  (a) insulin sensitizers including (i) PPARγ agonists such as the glitazones (e.g. troglitazone, pioglitazone, englitazone, MCC-555, rosiglitazone, and the like), and compounds disclosed in WO97/27857, 97/28115, 97/28137 and 97/27847; (ii) biguanides such as metformin and phenformin;
  (b) insulin or insulin mimetics;
  (c) sulfonylureas such as tolbutamide and glipizide, or related materials;
  (d) α-glucosidase inhibitors (such as acarbose);
  (e) cholesterol lowering agents such as (i) HMG-CoA reductase inhibitors (lovastatin, simvastatin and pravastatin, fluvastatin, atorvastatin, rivastatin and other statins), (ii) sequestrants (cholestyramine, colestipol and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and benzafibrate), (v) inhibitors of cholesterol absorption for example beta-sitosterol and (acyl CoA:cholesterol acyltransferase) inhibitors for example melinamide and (vi) probucol;

(f) PPARα/γ agonists;

(g) antiobesity compounds such as appetite suppressants, fenfluramine, dexfenfluramine, phentiramine, sulbitramine, orlistat, neuropeptide Y5 inhibitors (NP Y5 receptor antagonosts), leptin, which is a peptidic hormone, $\beta_3$ adrenergic receptor agonists, and PPARγ antagonists and partial agonists;

(h) ileal bile acid transporter inhibitors; and (i) insulin receptor activators.

Abbreviations

The following abbreviations have the indicated meanings:
Ac=acetyl
AIBN=2.2-azobisisobutyronitrile
Bn=benzyl
Bz=benzoyl
DIBAL=diisobutyl aluminum hydride
DAST=diethylamino sulfur trifluoride
DBU=diazabicyclo[5.4.0]undec-7-ene
DMAP=4-(dimethylamino)pyridine
DMF=N,N-dimethylformamide
DMSO=dimethyl sulfoxide
Et$_3$N=triethylamine
HBSS=Hanks balanced salt solution
HEPES=N$^1$-[2-Hydroxyethyl]piperazine-N$^4$-[2-ethanesulfonic acid]
KHMDS=potassium hexamethyldisilazide
KOtBu=potassium tert-butoxide
LHMDS=lithium hexamethyldisilazide
LDA=lithium diisopropylamide
LPS=lipopolysaccharide
mCPBA=metachloro perbenzoic acid
MMPP=magnesium monoperoxyphthalate
Ms=methanesulfonyl=mesyl
MsO=methanesulfonate=mesylate
NBS=N-bromosuccinimide
nBuLi=n-butyl lithium
tBuLi=t-butyl lithium
NCS=N-chlorosuccinimide
NIS=N-iodosuccinimide
Oxone®=potassium peroxymonosulfate
PTP=protein tyrosine phosphatase
r.t.=room temperature
rac.=racemic
Tf=trifluoromethanesulfonyl=triflyl
TFA=trifluoroacetic acid
TFAA=trifluoroacetic anhydride
TfO=trifluoromethanesulfonate=triflate
THF=tetrahydrofuran
TLC=thin layer chromatography
Ts=p-toluenesulfonyl=tosyl
TsO=p-toluenesulfonate=tosylate
Tz=1H (or 2H)-tetrazol-5-yl Alkyl Group Abbreviations Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl Dose Abbreviations bid=bis in die=twice daily
qid=quater in die=four times a day
tid=ter in die=three times a day Alkyl means linear, branched and cyclic structures, and combinations thereof, containing the indicated number of carbon atoms. Examples of alkyl groups include methyl, ethyl, propyl, isopropyl, butyl, s- and t-butyl, pentyl, hexyl, heptyl, octyl, nonyl, undecyl, dodecyl, tridecyl, tetradecyl, pentadecyl, eicosyl, 3,7-diethyl-2,2-dimethyl-4-propylnonyl, cyclopropyl, cyclopentyl, cycloheptyl, adamantyl, cyclododecylmethyl, 2-ethyl-1-bicyclo[4.4.0] decyl and the like.

Fluoroalkyl means alkyl groups of the indicated number of carbon atoms in which one or more hydrogens is replaced by fluorine. Examples are —CF$_3$, —CH$_2$CH$_2$F, —CH$_2$CF$_3$, c-Pr-F$_5$, c-Hex-F$_{11}$ and the like. Haloalkyl has the analogous meaning for replacement of one or more hydrogen atoms with any halogen (Cl, Br, F, and/or I).

Alkenyl means linear, branched and cyclic structures, and combinations thereof containing a double bond with the indicated number of carbon atoms. Examples of alkenyl groups include allyl, 2-butenyl, 3-butenyl,2-pentenyl, 2-cyclopentenyl, 3-cyclopentenyl, 2-methyl-cyclohexenyl, 2-cyclohexenyl, 3-cyclohexenyl and the like. Alkadienyl means the diunsaturated counterpart to alkenyl.

Alkynyl means linear, branched and cyclic structures, and combinations thereof containing a triple bond with the indicated number of carbon atoms. Examples of alkynyl groups include propargyl, 2-butynyl, 3-butynyl, 2-pentynyl, cyclopropylethynyl, and the like.

Alkylene, alkenylene, alkynylene, fluoroalkylene, alkadienylene, and the like, where the suffix "ene" has been added to the name of the monovalent radicals alkyl, alkenyl, alkynyl, fluoroalkyl, alkadienyl, and the like, describe divalent radicals that are the same as their monovalent counterparts, except that two hydrogen atoms rather than one are removed so that the radical will have two attachments.

Aryl means a 6–14 membered carbocyclic aromatic ring system comprising 1–3 phenyl rings. If two or more aromatic rings are present, then the rings are fused together, so that adjacent rings share a common side.

Heteroaryl (Het) as used herein represents a 5–10 membered aromatic ring system containing one ring or two fused rings, 1–4 heteroatoms, 0–4 of which are N atoms and 0–2 of which are O or $S(O)_y$, wherein y is as previously defined, and 0–2 carbonyl groups. Carbonyl groups, when present, are not counted as heteroatoms. Het includes, but is not limited to, furanyl, diazinyl, imidazolyl, isooxazolyl, isothiazolyl, oxadiazolyl, oxazolyl, pyrazolyl, pyridyl, pyrrolyl, tetrazinyl, thiazolyl, thienyl, triazinyl, triazolyl, 1H-pyrrole-2,5-dionyl, 2-pyrone, 4-pyrone, pyrrolopyridine, furopyridine and thienopyridine.

Benzoheteroaryl, which is a subset of Het includes aromatic ring systems containing one or more heteroatoms which also have a fused 6-membered benzene ring, such as 2H-1-benzopyran-2-one, 4H-1-benzopyran-4-one, 2(3H) benzofuranone, 3(2H)benzofuranone, 2,3-dihydrobenzofuran, 2,3-dihydrobenzothiophene, indole, benzofuran, benzothiophene, benzimidazole, benzoxazole, benzothiazole, benzotriazole, benzothiadiazole, 1H-isoindole-1,3(2H)-dione, quinoline, and isoquinoline.

Another subset of heteroaryls includes 5-membered heteroaryls, such as the following:

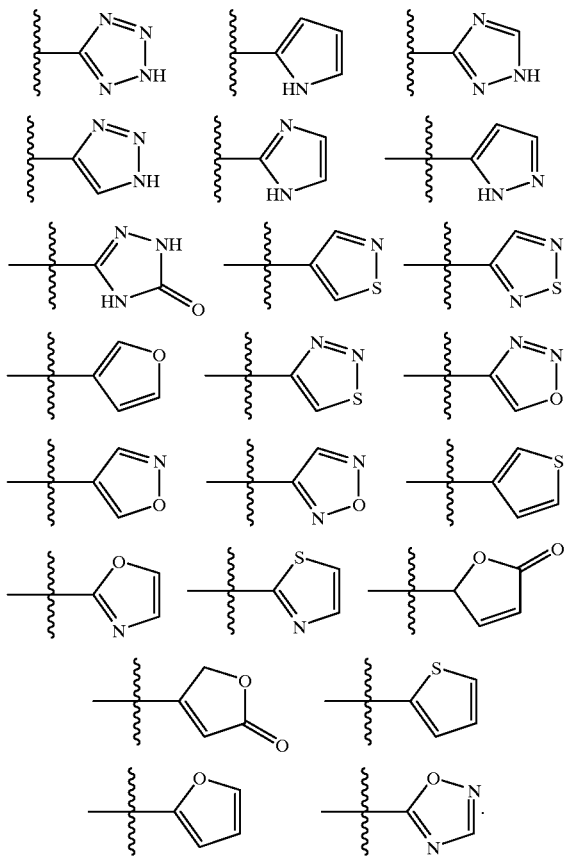

When a heteroaromatic ring is specified as optionally having one or more heteroatoms, this means that at least one heteroatom is present, selected from O, S and N, and up to 4 such heteroatoms may be present, depending upon the size of the ring specified.

When a moiety is specified as being optionally substituted, then the same moiety may also remain unsubstituted, unless otherwise stated.

Finally, when a list of possible choices is provided for a given moiety, and the moiety is used in more than one position in a chemical formula, the selection of a choice for the moiety in each position is independent of other selections, unless the definition says otherwise.

Metabolites—Prodrugs

Metabolites of the compounds of this invention that are therapeutically active and that are described by formula I also are within the scope of the claimed invention, as are prodrugs, which are compounds that are converted to the claimed compounds or salts of the claimed compounds after they have been administered to a patient. A non-limiting example of a prodrug of the phosphonic acids of this invention would be a monoester or diester of the phosphonic acid group, where the ester functionality has a structure that makes it easily hydrolyzed or metabolized after administration to a patient. Examples of such prodrugs are the compounds shown below, where R'=H or a $C_{1-6}$alkyl group, and R"=a $C_{1-6}$alkyl group or —$OC_{1-6}$alkyl group, where Q is the residue of the molecule that is attached to the —$CF_2PO_3H_2$ group in formula I. The alkyl groups and alkoxy groups may optionally be substituted with one or more substituents independently selected from 1–5 halogen atoms, a phenyl group, or a mixture of these. The phenyl group, if present, may optionally be substituted with 1–3 substituents independently selected from halogen, —$CH_3$, —$CF_3$, —$OCH_3$ and —$OCF_3$. In these compounds, and in general as defined throughout this application, the alkyl groups and the alkyl portions of Oalkyl groups may be linear or branched and may optionally be cycloalkyl or may include a cycloalkyl group in their structure. For examples of related prodrug structures, see D. N. Srinivasta et al., Bioorganic Chemistry 12, 118–129 (1984).

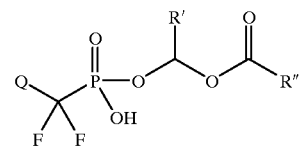

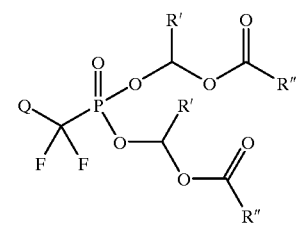

Other ester functionalities that may be used in the monoester or diester phosphonate prodrugs include phenyl esters and benzyl esters, where the phenyl ester groups have the structure —Ophenyl, and the benzyl ester groups have the structure —OCHR'phenyl, in which R' is H or $C_{1-6}$alkyl, and $C_{1-6}$alkyl is substituted as described above. In either case, phenyl is substituted as described above.

The prodrugs of this invention may therefore be defined as compounds having the formula Ia shown below:

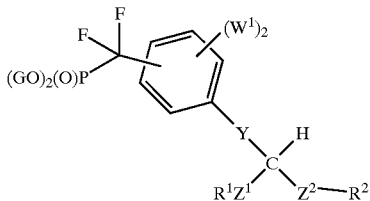

Ia

In the compound having Formula Ia, one group G is independently selected from H, phenyl, —CHR'phenyl, and —CHR'OC(=O)R", and one group G is selected from phenyl, —CHR'phenyl and —CHR'OC(=O)R", where each group R' is H or $C_{1-6}$alkyl and each group R" is —$C_{1-6}$alkyl or —$OC_{1-6}$alkyl, where $C_{1-6}$alkyl and the alkyl portion of —$OC_{1-6}$alkyl may optionally be substituted with one or more substituents independently selected from 1–5 halogen atoms, a phenyl group, or a mixture of these. The phenyl group in —CHR'phenyl, the phenyl group that is an optional substituent on $C_{1-6}$alkyl and —$OC_{1-6}$alkyl, and the phenyl ester group, where G is phenyl, may optionally be substituted with 1–3 groups independently selected from halogen, —$CH_3$, —$CF_3$, —$OCH_3$ and —$OCF_3$. By this definition, the phosphonic acid group is a monoester or diester. In preferred compounds, the groups G that are not H in diesters are the same because of the difficulty of synthesizing different G groups on the same phosphonate.

Optical Isomers—Diastereomers—Geometric Isomers

Some of the compounds described herein contain one or more asymmetric centers and may thus give rise to diastereomers and enantiomers, which in turn can be resolved as optical isomers. The present invention includes all such diastereomers and enantiomers, including racemic mixtures and resolved, enantiomerically pure forms, and pharmaceutically acceptable salts thereof. Some of the compounds described herein contain olefinic double bonds, and unless specified otherwise, include both E and Z geometric isomers.

Salts

The pharmaceutical compositions of the present invention comprise a compound of the current invention as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable acids, including inorganic and organic acids. Such acids include acetic, adipic, aspartic, 1,5-naphthalenedisulfonic, benzenesulfonic, benzoic, camphorsulfonic, citric, 1,2-ethanedisulfonic, ethanesulfonic, ethylenediaminetetraacetic, fumaric, glucoheptonic, gluconic, glutamic, hydriodic, hydrobromic, hydrochloric, isethionic, lactic, maleic, malic, mandelic, methanesulfonic, mucic, 2-naphthalenesulfonic, nitric, oxalic, pamoic, pantothenic, phosphoric, pivalic, propionic, salicylic, stearic, succinic, sulfuric, tartaric, p-toluenesulfonic acid, undecanoic, 10-undecenoic, and the like. Particularly preferred are citric, hydrobromic, hydrochloric, maleic, methanesulfonic, phosphoric, sulfuric and tartaric acids.

It will be understood that in the discussion of methods of treatment or of specific compounds which follows, references to the compounds of Formula I and other formulae are meant to include the pharmaceutically acceptable salts.

Utilities

Inhibitors of PTP-1B improve insulin-sensitivity and thus have utility in preventing or treating Type 1 and Type 2 diabetes, improving glucose tolerance and insulin-sensitivity when there is insulin-resistance, and in treating or preventing obesity, all in mammals that are in need of such treatments or that might benefit from such treatments. The compounds also exhibit a beneficial reduction in triglycerides and lipids. Compounds in the present class of phosphonic acids are advantageous over known phosphonic acids previously investigated as candidate PTP 1B inhibitors. The compounds of this invention show improved pharmacokinetics when compared with known phosphonates. These compounds are active in intact cell-based assays.

The PTP-1B inhibitors may also be useful in the treatment, prevention or control of a number of conditions that accompany type 2 diabetes, including hyperlipidemia, hypertriglyceridemia, hypercholesterolemia (including beneficially raising low HDL levels), atherosclerosis, vascular restenosis, pancreatitis, adipose cell tumors, adipose cell carcinomas such as liposarcoma, dyslipidemia, inflammatory bowel disease, inflammation in general, and other disorders where insulin resistance is a component. Finally, the compounds may be used to treat or prevent cancer, such as prostate cancer, neurodegenerative diseases and the like.

Pharmaceutical Compositions

For the treatment of any of these PTP-1B-mediated diseases the active compound may be administered orally, topically, parenterally, by inhalation spray or rectally in dosage units containing conventional pharmaceutically acceptable carriers. The term parenteral as used herein includes subcutaneous, intravenous, intramuscular and intrasternal injection and infusion techniques. In addition to the treatment of warm-blooded animals such as mice, rats, horses, cattle, sheep, dogs, cats, etc., the compounds of the invention are useful for the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, coloring agents and preserving agents in order to provide pharmaceutically elegant and palatable preparations. Tablets contain the active ingredient in admixture with pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and coloring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxy-ethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and coloring agents. The pharmaceutical composition may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a parenterally-acceptable diluent or solvent, for example as a solution in 1,3-butanediol. Examples of vehicles and solvents include water, Ringer's solution and isotonic sodium chloride. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds may also be administered in the form of suppositories. These compositions can be prepared by mixing the drug with a suitable non-irritating excipient which is solid at ordinary temperatures but molten at the body temperature and will therefore release the drug. Such materials include cocoa butter and polyethylene glycols.

For topical use, creams, ointments, gels, solutions or suspensions containing the compound are employed. (For purposes of this application, topical application includes mouth washes and gargles.) Topical formulations may include cosolvents, emulsifiers, penetration enhancers, preservatives,emollients and the like.

The pharmaceutical composition may also be further comprised of a second anti-diabetic or anti-obesity effective compound.

Dose Ranges

Dosage levels on the order of from about 0.01 mg to about 100 mg/kg of body weight per day are useful in the treatment of the above-indicated conditions, or alternatively about 0.5 mg to about 7 g per patient per day. For example, the diseases and conditions described herein may be effectively treated by the administration of from about 0.01 to 50 mg of the compound per kilogram of body weight per day, or alternatively about 0.5 mg to about 3.5 g per patient per day.

The active ingredient is typically combined with the carrier to produce a dosage form suitable for the particular patient being treated and the particular mode of administration. For example, a formulation intended for the oral administration of humans may contain from about 0.5 mg to about 5 g of the active agent, compounded with an appropriate and convenient amount of carrier material which may vary from about 5 to about 95 percent of the total composition. Representative dosage forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It is understood that the specific dose level for any particular patient will depend upon a variety of factors including the age, body weight, general health, sex, diet, time of administration, route of administration, rate of excretion, drug combination and the severity of the particular disease undergoing therapy.

Combinations with Other Drugs

In further aspects, the invention encompasses pharmaceutical compositions for treating PTP-1B mediated diseases as defined above comprising an effective amount of the active compound and one or more other pharmaceutically active compounds, such as anti-diabetic compounds (for example, insulin, sulfonyl ureas, PPAR-alpha and/or -gamma ligands, including ligands that have both PPAR-alpha and -gamma activity), anti-obesity compounds, and compounds that improve the lipid profile of the patient.

Thus, the methods of treatment or prevention described herein may further be comprised of administering to said patient a second anti-diabetic compound in an amount effective to treat, control, or prevent diabetes, alone or in combination with the PTP-1B inhibitors of this invention.

Similarly, the methods of treatment or prevention described herein may further be comprised of administering to said patient an anti-obesity compound in an amount effective to treat, control or prevent obesity, alone or in combination with the PTP-1B inhibitors of this invention.

Similarly, the methods of treatment of diabetes may comprise the administration of a cholesterol biosynthesis inhibitor, particularly an HMG-CoA reductase inhibitor, such as lovastatin, simvastatin, pravastatin, fluvastatin, atorvastatin and rivastatin, in an amount effective to improve the lipid profile. In combination with a PTP-1B inhibitor, this may be beneficial in treating or preventing atherosclerosis and other conditions that often are associated with Type 2 diabetes.

Examples of other pharmaceutically active compounds that may be combined with a compound of Formula I and administered in combination with the PTP-1B inhibitors include, but are not limited to, the following compounds or compositions or groups of compounds or compositions that are used as anti-diabetes compounds (a, b, c, d, f, and i below), anti-obesity compounds (g below), and /or compounds or compositions for lipid profile control (e and h below):

(a) insulin sensitizers including (i) PPARγ agonists such as the glitazones (e.g. troglitazone, pioglitazone, englitazone, MCC-555, rosiglitazone, and the like), and compounds disclosed in WO97/27857, 97/28115, 97/28137 and 97/27847; (ii) biguanides such as metformin and phenformin;

(b) insulin or insulin mimetics;

(c) sulfonylureas such as tolbutamide and glipizide, or related materials;

(d) α-glucosidase inhibitors (such as acarbose);

(e) cholesterol lowering agents such as (i) HMG-CoA reductase inhibitors (lovastatin, simvastatin and pravastatin, fluvastatin, atorvastatin, rivastatin and other statins), (ii) sequestrants (cholestyramine, colestipol and a dialkylaminoalkyl derivatives of a crosslinked dextran), (iii) nicotinyl alcohol, nicotinic acid or a salt thereof, (iv) PPARα agonists such as fenofibric acid derivatives (gemfibrozil, clofibrate, fenofibrate and benzafibrate), (v) inhibitors of cholesterol absorption such as for example beta-sitosterol and acyl CoA-:cholesterol acyltransferase inhibitors such as for example melinamide, and (vi) probucol;

(f) PPARα/γ agonists;

(g) antiobesity compounds such as appetite suppressants, fenfluramine, dexfenfluramine, phentiramine, sulbitramine, orlistat, neuropeptide Y5 inhibitors (NP Y5 receptor antagonosts), leptin, which is a peptidic hormone, $\beta_3$ adrenergic receptor agonists, and PPARγ antagonists and partial agonists;

(h) ileal bile acid transporter inhibitors; and (i) insulin receptor activators, such as those disclosed in copending, commonly assigned U.S. application Ser. Nos. 09/095,244 and 09/280,602.

Where a second pharmaceutical is used in addition to an active compound taught herein, the two pharmaceuticals may be administered together in a single composition, separately at approximately the same time, or on separate dosing schedules. The important feature is that their dosing schedules comprise a treatment plan in which the dosing schedules overlap in time and thus are being followed concurrently.

Methods of Synthesis

The compounds of the present invention can be prepared according to the following methods.

METHOD A

Toluic acid derivative 1 can be treated with NBS in 1,2-dichloroethane with AIBN under light at reflux to give bromide 2. The acid can be reduced with borane in THF to provide the alcohol 3 which in turn is oxidized with $MnO_2$ to afford aldehyde 4. Di-tert-butyl phosphite can be deprotonated with a base such as $LiN(TMS)_2$ and reacted with aldehyde 4. The resulting alcohol 5 is then oxidized with $MnO_2$ to provide ketone 6. The ketone 6 is treated with DAST to afford compound 7.

Method A

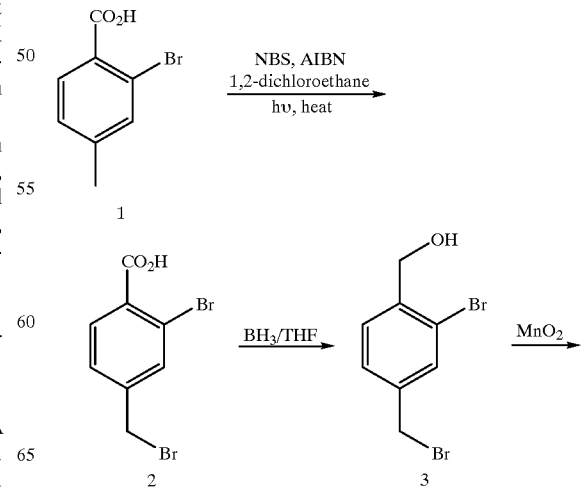

-continued

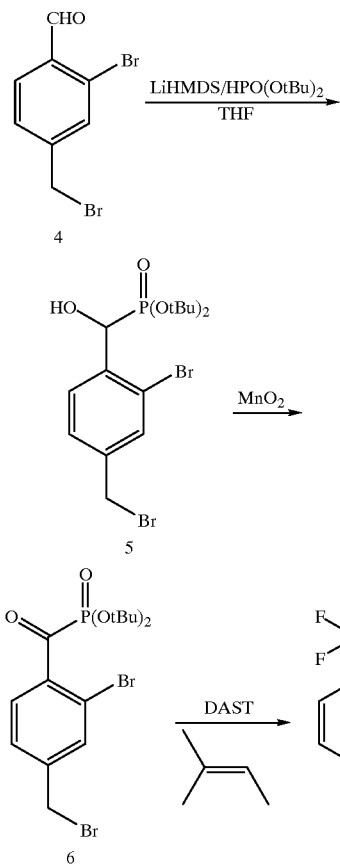

METHOD A-1

The methyl ester of 4-aminobenzoic acid II can be brominated with pyridinium tribromide to give III, which is treated with NaNO$_2$/HCl and KCN/CuCN to give nitrile IV. DIBAL reduction followed by bromination with POBr$_3$, gives VI, which is treated with lithium dialkyl phosphite to afford the phosphonate alcohol VII. Swern oxidation followed by fluorination with DAST provide the desired difluoromethyl phosphonate IX.

Method A-1

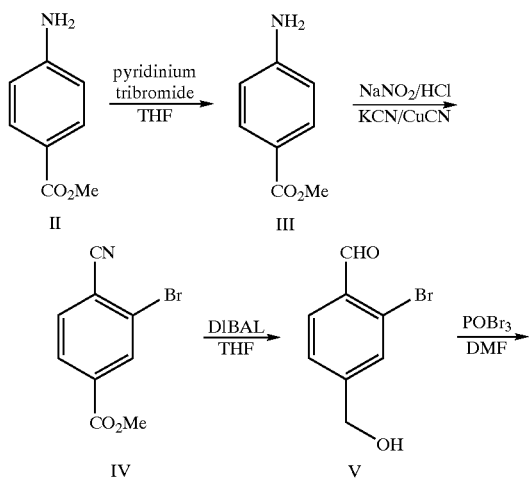

-continued

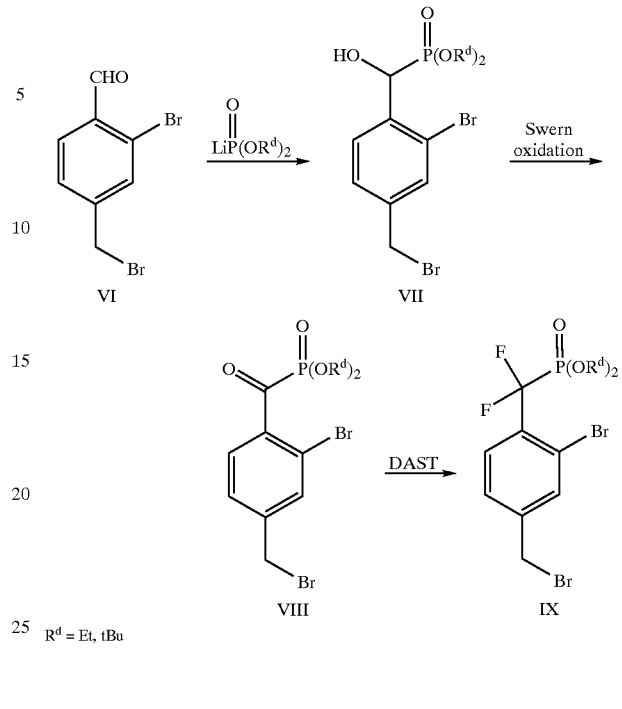

R$^d$ = Et, tBu

METHOD B

α-Bromo-p-tolunitrile is reduced with DIBAL to provide aldehyde 9. Di-tert-butyl phosphite can be deprotonated with a base such as LHMDS and reacted with aldehyde 9 to provide alcohol 10. Alcohol 10 can be oxidized with MnO$_2$ to afford ketone 11 which in turn is treated with DAST to give 12.

Method B

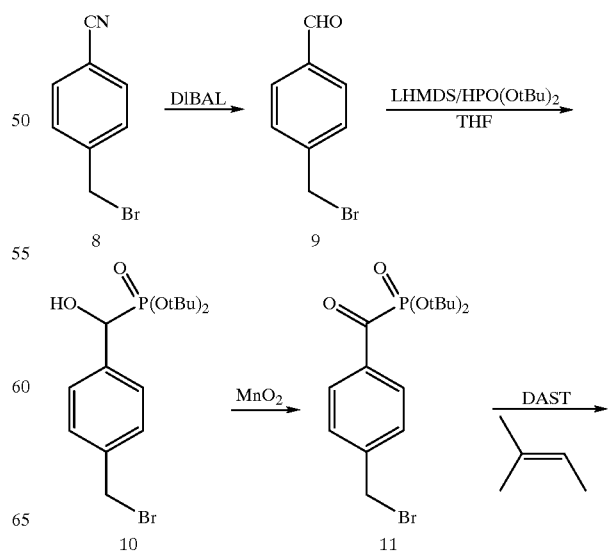

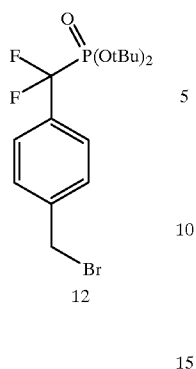

12

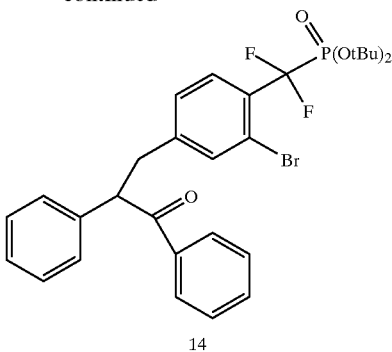

14

| HOAc/H₂O

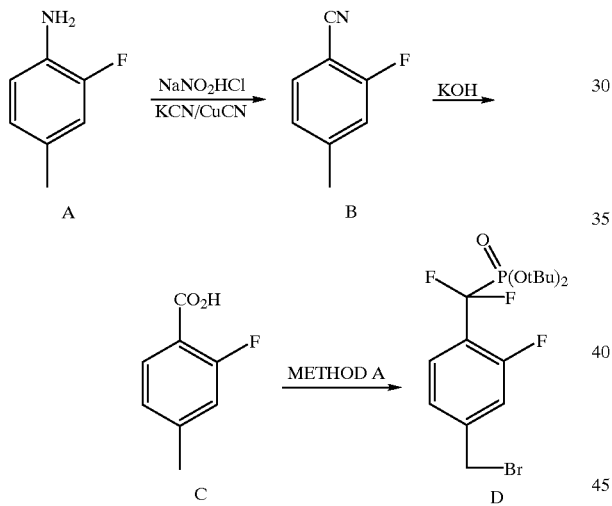

15

METHOD B-1

2-Fluoro-4-methyl aniline A is treated with $NaNO_2$/HCl followed by KCN/CuCN to give nitrile B which in turn is hydrolyzed to give C. Compound C is converted to D using sequence described in Method A. This sequence can also be applied to the ortho chloro analog.

Method B-1

METHOD D

Template 16 is treated with a suitable base such as NaH, KOtBu, LHMDS, KHMDS, LDA, nBuLi, tBuLi or a combination of these, and the anion is alkylated with 17 to provide 18 which is then deprotected with acid to provide the desired compound I.

METHOD C

Deoxybenzoin 13 can be deprotonated with potassium tert-butoxide and treated with compound 7 to give 14 (A similar alkylation can be performed using compound 12.) The ester is then hydrolyzed with AcOH-H₂O to give acid 15.

Method C

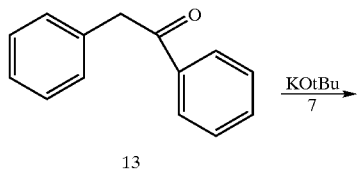

13

Method D

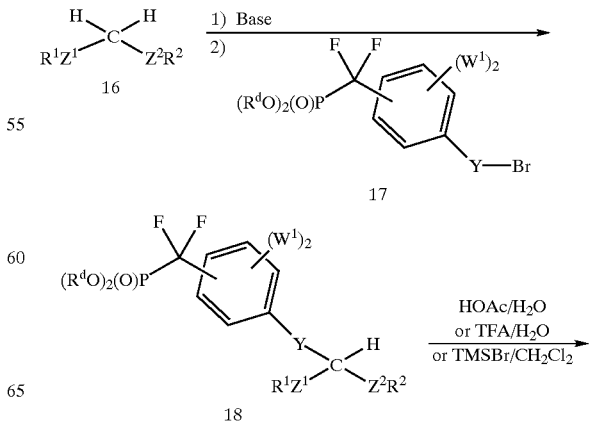

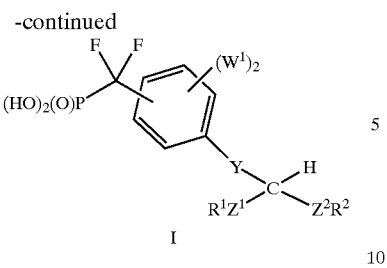

$R^d$ = tBu, Et

METHOD E

The disodium phosphonate 19 can be alkylated with a chloroalkyl ester (*Synth. Com.* 25(18) 2739 (1995)) or carbonate (*Antiviral Chemistry & Chemotherapy* 8, 557 (1997)) to give both the mono and diprotected phosphonates which can be separated by flash chromatography on silica gel. Q is the residue of the molecule that is attached to the —$CF_2PO_3H_2$ group.

Method E

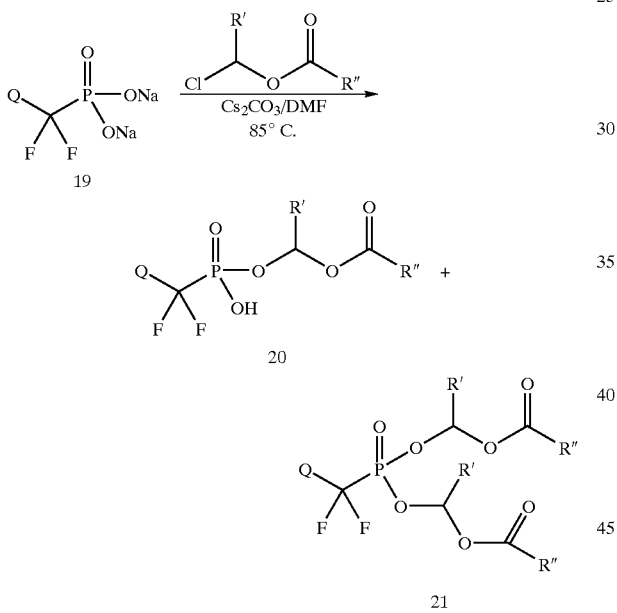

METHOD F

The phosphonic acid 22 can be treated with $Cs_2CO_3$ and a chloroalkyl ester or carbonate in $CH_3CN$ to give a mixture of mono and diprotected phosphonates which can be separated by flash chromatography on silica gel. Q is the residue of the molecule that is attached to the —$CF_2PO_3H_2$ group.

Method F

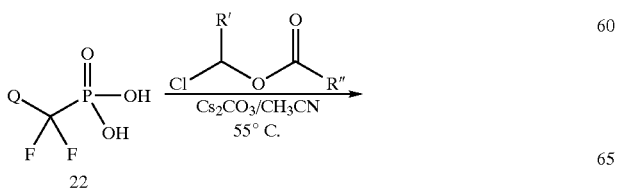

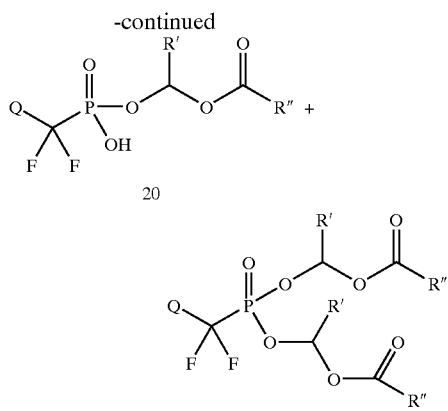

METHOD G

The phosphonic acid 22 can be treated with silver trifluoroacetate to give the disilver salt 23 which can be treated with an iodoalkyl ester (*Eur. J. Phar. Sci.* 4, 49 (1996)) or carbonate to give a mixture of the mono and diprotected phosphonates which are separable by flash chromatography. This method can also be used to obtain the benzyl ester using benzyl bromide as alkylating agent. Q is the residue of the molecule that is attached to the —$CF_2PO_3H_2$ group.

Method G

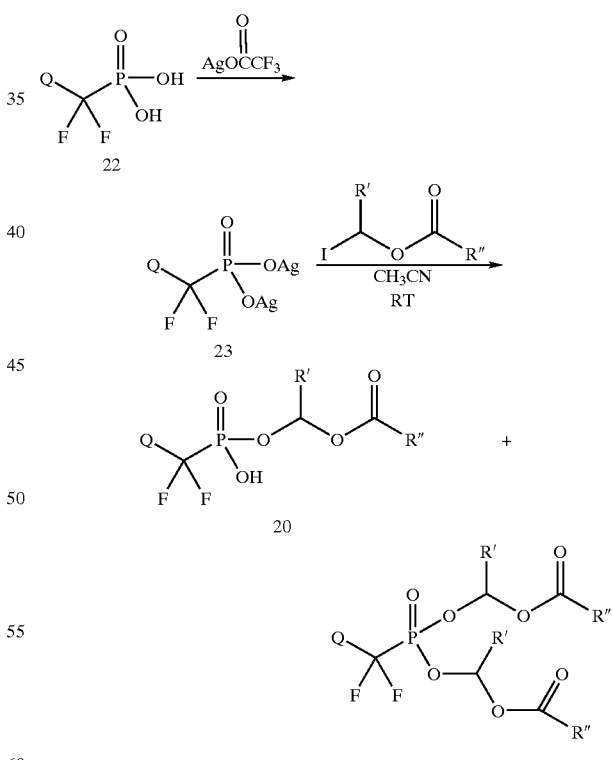

METHOD H

Benzonitrile 24 can be treated with hydroxylamine hydrochloride to give 25. Compound 25 can be treated with phenyl acetic acid to afford compound 26 which in turn is alkylated with 7 from Method A to provide 27. The free acid 28 is obtained by treatment of 27 with an acid.
Method H
A and a base to provide 32. The free acid 33 can be obtained from 32 by acid treatment.
Method I
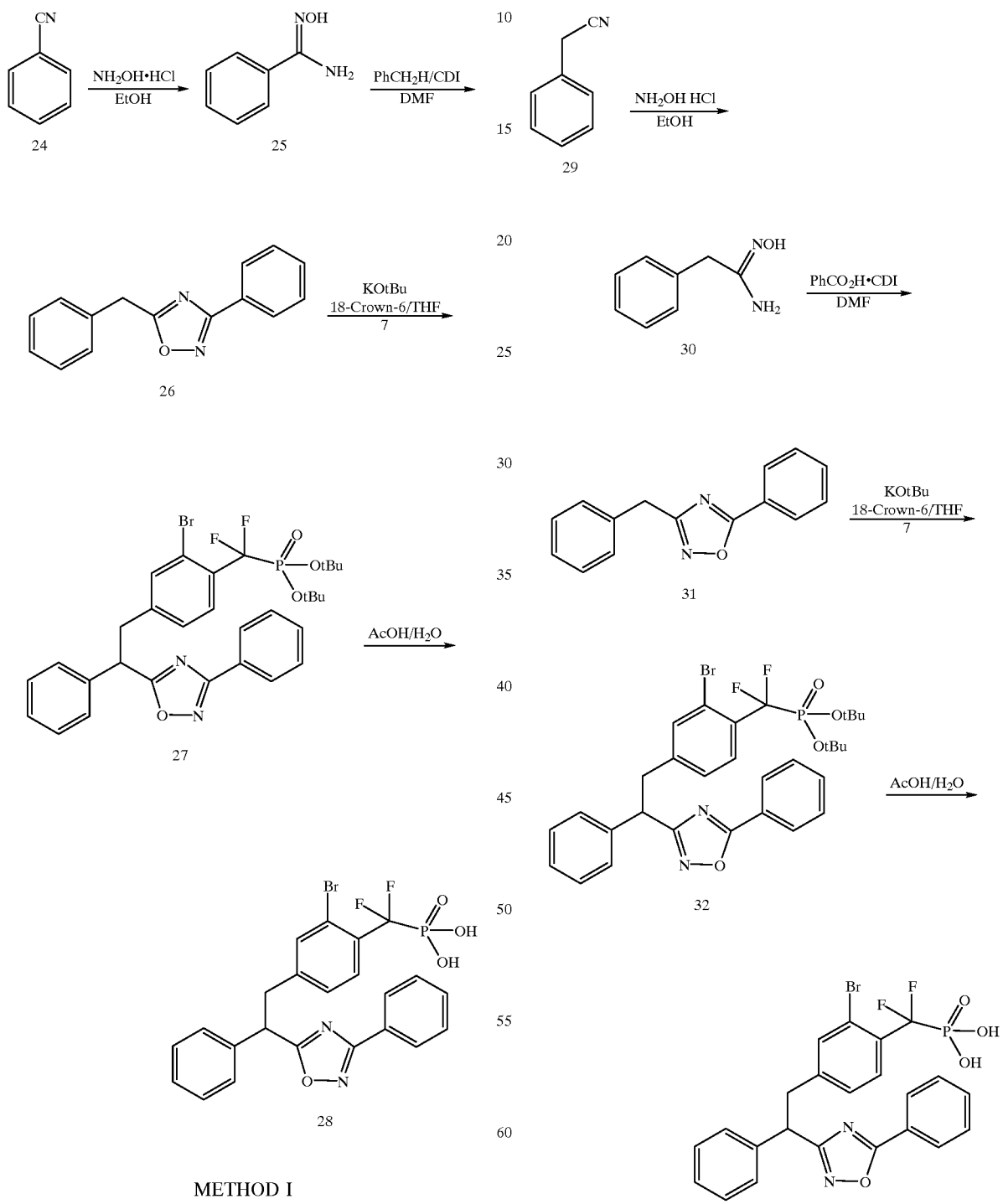
METHOD I
Benzyl nitrile 29 can be treated with hydroxylamine to give 30. Compound 30 can react with phenylacetic acid to afford 31 which in turn can be alkylated with 7 from Method TABLE 1
Structures of Examples
| | Example | Method |
|---|---|---|
| 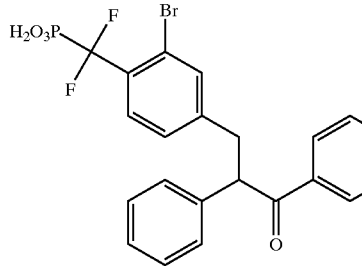 | 1 | A + C |
| 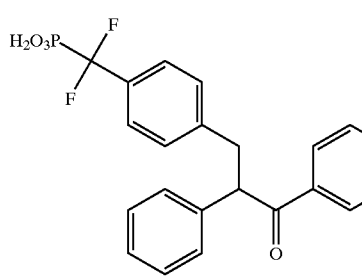 | 2 | B + C |
| 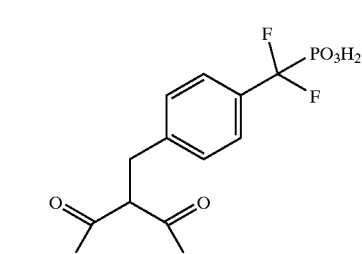 | 3 | B + D |
| 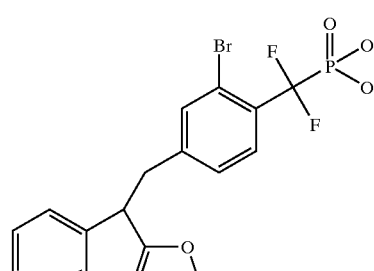 | 4 | A + I + D |

TABLE 1-continued

Structures of Examples

| Structure | Example | Method |
|---|---|---|
| (structure 5) | 5 | A + H + D |
| (structure 6) | 6 | B + D |
| (structure 7) | 7 | A + D |
| (structure 8) | 8 | B + D |

TABLE 1-continued

Structures of Examples

| Structure | Example | Method |
|---|---|---|
| (structure with benzotriazole, difluoromethylphosphonic acid, and methyl benzoate groups) | 9 | B + D |
| (structure with benzotriazole, 4-CF$_2$PO$_3$H$_2$-phenyl, and 4-fluorophenyl groups) | 10 | B + D |
| (structure with benzotriazole, 4-CF$_2$PO$_3$H$_2$-phenyl, and phenyl groups) | 11 | B + D |
| (structure with 3-Br-4-CF$_2$PO(OH)(OCH$_2$OC(O)C(CH$_3$)$_3$)-phenyl, phenyl, and benzoyl groups) | 12 | A + C + F |
| (structure with 3-Br-4-CF$_2$PO(OCH$_2$OC(O)C(CH$_3$)$_3$)$_2$-phenyl, phenyl, and benzoyl groups) | 13 | A + C + G |

TABLE 1-continued

Structures of Examples

| Example | Method |
|---|---|
| 14 | A + C + F |
| 15 | A + C + G |
| 16 | A + C + G |
| 17 | A + C + G |

TABLE 1-continued
Structures of Examples
| | Example | Method |
|---|---|---|
| 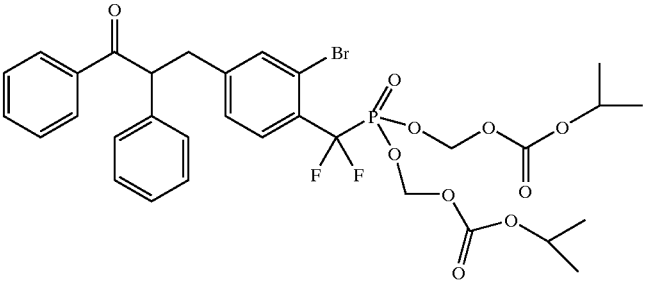 | 18 | A + C + G |
| 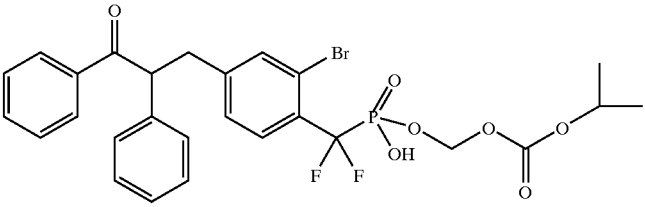 | 19 | A + C + G |
| 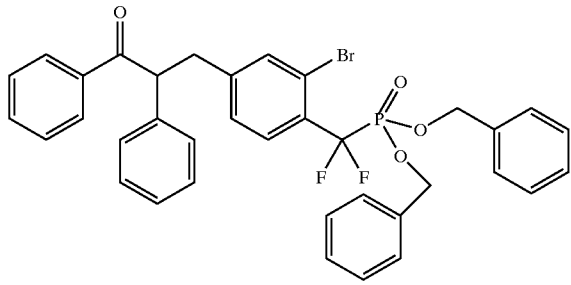 | 20 | A + C + G |
| 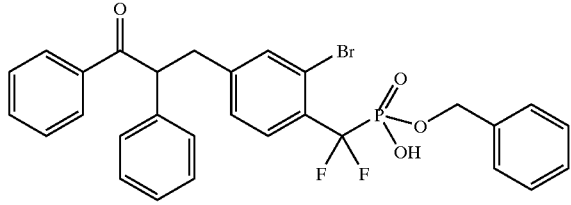 | 21 | A + C + G |
| 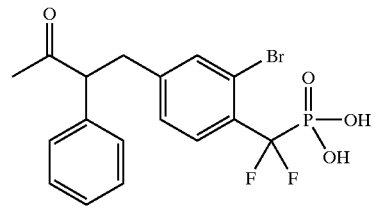 | 22 | A + D |
| 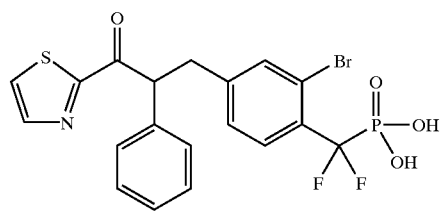 | 23 | A + D |

TABLE 1-continued
Structures of Examples
| | Example | Method |
|---|---|---|
| | 24 | A + D |
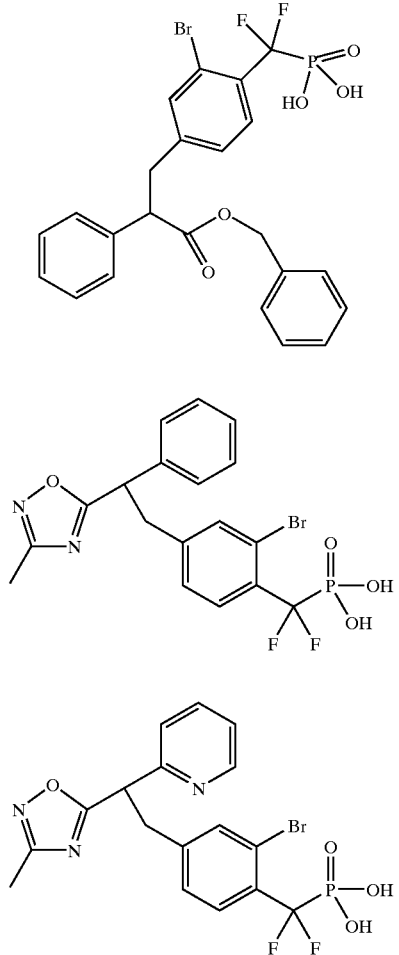
TABLE 2
Other Structures of the Invention
TABLE 2-continued
Other Structures of the Invention
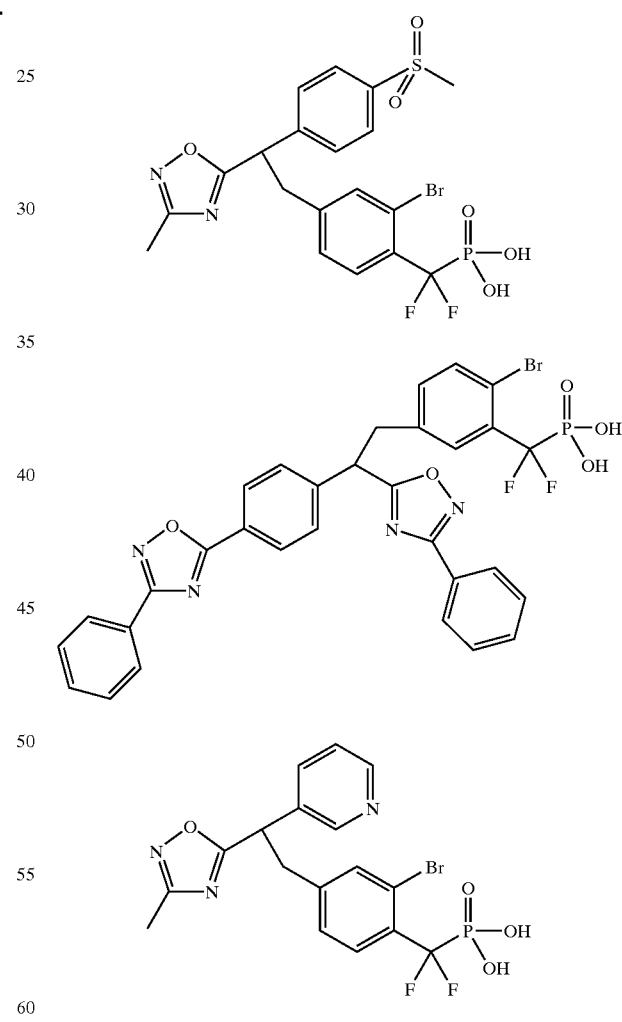

TABLE 2-continued

Other Structures of the Invention

[Chemical structure: A compound with (HO)₂P(=O)-CF₂- group attached to a fluorinated phenyl ring, connected via CH₂ to a CH(phenyl)-C(=O)-phenyl moiety]

Assays for Demonstrating Biological Activity

Activity in the compounds of this application is demonstrated using the following assays for PTP-1B-inhibiting activity.

Phosphatase Assay Protocol

Materials:
  EDTA-ethylenediaminetetraacetic acid (Sigma)
  DMH-N,N'-dimethyl-N,N'-bis(mercaptoacetyl)-hydrazine (synthesis published in *J. Org. Chem.* 56, pp. 2332–2337, (1991) by R. Singh and G. M. Whitesides and can be substituted with DTT-dithiothreitol Bistris-2,2-bis (hydroxymethyl)2,2',2"-nitrilotriethanol-(Sigma) Triton X-100-octylphenolpoly(ethylene-glycolether) 10 (Pierce)
  Antibody: Anti-glutathione S-transferase rabbit (H and L) fraction (Molecular Probes)
  Enzyme: Human recombinant PTP-1B, containing amino acids 1 –320, fused to GST enzyme (glutathione S-transferase) or to FLAG peptide purified by affinity chromatography (Huyer et al, 1997, *J. Biol. Chem.*, 272, 843–852). Wild type contains active site cysteine(215), whereas mutant contains active site serine(215).
  Tritiated peptide: Bz-NEJJ-CONH₂, Mwt. 808, empirical formula, $C_{32}H_{32}T_2O_{12}P_2F_4$
Stock Solutions

| Stock Solutions | |
|---|---|
| (10X) Assay Buffer | 500 mM Bistris (Sigma), pH 6.2, MW = 209.2 |
| | 20 mM EDTA (GIBCO/BRL) |
| | Store at 4° C. |
| Prepare fresh daily: | |
| Assay Buffer (1X) | 50 mM Bistris |
| (room temp.) 2 mM EDTA | |
| | 5 mM DMH (MW = 208) |
| Enzyme Dilution | |
| Buffer (keep on ice) | 50 mM Bistris |
| | 2 mM EDTA |
| | 5 mM DMH |
| | 20% Glycerol (Sigma) |
| | 0.01 mg/ml Triton X-100 (Pierce) |
| Antibody Dilution | |
| Buffer (keep on ice) | 50 mM Bistris |
| | 2 mM EDTA |

IC₅₀ Binding Assay Protocol

Compounds (ligands) which potentially inhibit the binding of a radioactive ligand to the specific phosphatase are screened in a 96-well plate format as follows:

To each well is added the following solutions @25° C. in the following chronological order:

1. 110 μl of assay buffer.
2. 10 μl. of 50 nM tritiated BzN-EJJ-CONH₂ in assay buffer (1×) @25° C.
3. 10 μl. of testing compound in DMSO at 10 different concentrations in serial dilution (final DMSO, about 5% v/v) in duplicate @25° C.
4. 10 μl. of 3.75 μg/ml purified human recombinant GST-PTP-1B in enzyme dilution buffer.
5. The plate is shaken for 2 minutes.
6. 10 μl. of 0.3 μg/ml anti-glutathione S-transferase (anti-GST) rabbit IgG (Molecular Probes) diluted in antibody dilution buffer @25° C.
7. The plate is shaken for 2 minutes.
8. 50 μl. of protein A-PVT SPA beads (Amersham) @25° C.
9. The plate is shaken for 5 minutes. The binding signal is quantified on a Microbeta 96-well plate counter.
10. The non-specific signal is defined as the enzyme-ligand binding in the absence of anti-GST antibody.
11. 100% binding activity is defined as the enzyme-ligand binding in the presence of anti-GST antibody, but in the absence of the testing ligands with the non-specific binding subtracted.
12. Percentage of inhibition is calculated accordingly.
13. IC₅₀ value is approximated from the non-linear regression fit with the 4-parameter/multiple sites equation (described in: "Robust Statistics", New York, Wiley, by P. J. Huber (1981) and reported in nM units.
14. Test ligands (compounds) with larger than 90% inhibition at 10 μM are defined as actives.

Enzyme Assay PTP-1B

Assay buffer 50 mM Bis-Tris (pH=6.3)
  2 mM EDTA
  5 mM N,N'-dimethyl-N,N'-bis(mercaptoacetyl)hydrazine (DMH)
Substrate 10 mM fluorescein diphosphate (FDP) store at −20°C
Enzyme dilution buffer 50 mM Bis-Tris (pH=6.3)
  2 mM EDTA
  5 mM DMH
  20 %(v/v) glycerol
  0.01% Triton X-100

The assay was carried out at room temperature in 96 well plates. The reaction mixture in 170 μl contained 50 mM Bis-Tris (pH=6.3), 2 mM EDTA, 5 mM N,N'-dimethyl-N, N'bis(mercaptoacetyl)hydrazine (DMH) and 10 μM fluorescein diphosphare (FDP). 10 μl of 10 concentrations (serial dilution) of the test compound (inhibitor) dissolved in DMSO or DMSO alone for control was added to each well and the plate was mixed for 2 min. The reaction was initiated by adding 20 μl of diluted PTP-1B (50 nM in 50 mM Bis/Tris (pH=6.3), 2 mM EDTA, 5 mM DMH, 20 % glycerol and 0.01% Triton X-100. The phosphatase activity was followed by monitoring the appearance of the fluorescent product fluorescein monophosphate (FMP) continuously for 15–30 min, using the Cytofluor II plate reader (PerSeptive Biosystems Inc.) with excitation of 440 nm (slit width 20 nm) and emission at 530 nm (slit width 25 nm). All the assays were done at least in duplicate. The initial rate of FMP formation is plotted against the concentration of inhibitor and the data was fitted to 4-parameter equation and the inflection point of the fit is the $IC_{50}$.

PHARMACOKINETICS IN RATS

Per Os Pharmacokinetics in Rats

PROCEDURE

The animals are housed, fed and cared for according to the Guidelines of the Canadian Council on Animal Care.

Male Sprague Dawley rats (325–375 g) are fasted overnight prior to each PO blood level study.

The rats are placed in the restrainer one at a time and the box firmly secured. The zero blood sample is obtained by nicking a small (1 mm or less) piece off the tip of the tail. The tail is then stroked with a firm but gentle motion from the top to the bottom to milk out the blood. Approximately 1 mL of blood is collected into a heparinized vacutainer tube.

Compounds are prepared as required, in a standard dosing volume of 10 mL/kg, and administered orally by passing a 16 gauge, 3" gavaging needle into the stomach.

Subsequent bleeds are taken in the same manner as the zero bleed except that there is no need to nick the tail again. The tail is cleaned with a piece of gauze and milked/stroked as described above into the appropriately labelled tubes.

Immediately after sampling, blood is centrifuged, separated, put into clearly marked vials and stored in a freezer until analysed.

Typical time points for determination of rat blood levels after PO dosing are:

0, 15 min, 30 min, 1 h, 2 h, 4 h, 6 h

After the 4 hr time point bleed, food is provided to the rats ad libitum. Water is provided at all times during the study.

Vehicles

The following vehicles may be used in PO rat blood level determinations:

| | |
|---|---|
| PEG 200/300/400: | restricted to 2 mL/kg |
| Methocel 0.5%–1.0%: | 10 mL/kg |
| Tween 80: | 10 mL/kg |

Compounds for PO blood levels can be in suspension form. For better dissolution, the solution can be placed in a sonicator for approximately 5 minutes.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug.

Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv(mg/kg)}{AUCiv}$$

The units of CL are mL/h·kg (milliliters per hour kilogram)

Intravenous Pharmacokinetics in Rats

PROCEDURE

The animals are housed, fed and cared for according to the Guidelines of the Canadian Council on Animal Care.

Male Sprague Dawley (325–375 g) rats are placed in plastic shoe box cages with a suspended floor, cage top, water bottle and food.

The compound is prepared as required, in a standard dosing volume of 1 mL/kg.

Rats are bled for the zero blood sample and dosed under $CO_2$ sedation. The rats, one at a time, are placed in a primed $CO_2$ chamber and taken out as soon as they have lost their righting reflex. The rat is then placed on a restraining board, a nose cone with $CO_2$ delivery is placed over the muzzle and the rat restrained to the board with elastics. With the use of forceps and scissors, the jugular vein is exposed and the zero sample taken, followed by a measured dose of compound which is injected into the jugular vein. Light digital pressure is applied to the injection site, and the nose cone is removed. The time is noted. This constitutes the zero time point.

The 5 min bleed is taken by nicking a piece (1–2 mm) off the tip of the tail. The tail is then stroked with a firm but gentle motion from the top of the tail to the bottom to milk the blood out of the tail. Approximately 1 ML of blood is collected into a heparinized collection vial. Subsequent bleeds are taken in the same fashion, except that there is no need to nick the tail again. The tail is cleaned with a piece of gauze and bled, as described above, into the appropriate labelled tubes.

Typical time points for determination of rat blood levels after I.V. dosing are either:

0, 5 min, 15 min, 30 min, 1 h, 2 h, 6 h or 0, 5 min, 30 min, 1 h, 2 h, 4 h, 6 h.

Vehicles

The following vehicles may be used in IV rat blood level determinations:

| | |
|---|---|
| Dextrose: | 1 mL/kg |
| 2-Hydroxypropyl-b-cyclodextrin | 1 mL/kg |
| DMSO (dimethylsulfoxide): | Restricted to a dose volume of 0.1 mL per animal |
| PEG 200: | Not more than 60% mixed with 40% sterile water - 1 mL/kg |

With Dextrose, either sodium bicarbonate or sodium carbonate can be added if the solution is cloudy.

For analysis, aliquots are diluted with an equal volume of acetonitrile and centrifuged to remove protein precipitate.

The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv(mg/kg)}{AUCiv}$$

The units of CL are mL/h·kg (milliliters per hour kilogram).

PTP 1B Intact Cell Assay

This assay is the subject of copending, commonly assigned U.S. Provisional Application No. 60/123,243, filed Mar. 8, 1999, which patent application is incorporated herein by reference, and was recently published in Cromlish, Wanda A., Paul Payette and Brian P. Kennedy (1999) *Biochem Pharmocol* 58: 1539–1546.

Construction of Recombinant Baculovirus Transfer Vectors And Insect Cells

Briefly, using the Bac-to-Bac Baculovirus Expression System (Gibco-BRL, Mississauga, Ontario, Canada) PTP 1B cDNA (obtained from Dr. R. L. Erikson, Harvard University, USA), is cloned into the pFASTBAC donor plasmid engineered to include a FLAG sequence at the 5' end of the cDNA (PTP1B-FL). The recombinant plasmid is transformed into competent DH10BAC *E. Coli* cells. Following transposition and antibiotic selection, the recombinant bacmid DNA is isolated from selected *E. Coli* colonies and used to transfect sf9 insect cells (Invitrogen, San Diego, Calif., U.S.A.). The sf9 cells are cultured in spinner flasks at 28° C. in Graces supplemented medium (Gibco-BRL, Mississauga, Ontario, Canada) with 10% heat-inactivated fetal bovine serum (Gibco-BRL) following the protocol of Summers and Smith (*A manual for Methods for Baculovirus Vectors and Insect Culture Procedures* (Bulletin No. 1555). Texas A & M University, Texas Agricultural Experiment Station, College Station, Tex., 1987).

Intact Cell Assay

Infected sf9 cells expressing PTP1B-FL and mock infected cells, are harvested at 29 hpi (hours post infection) by gentle centrifugation (Beckman GS-6R) at 460 rpm, (48 g) for 5 min. Cells are washed once in assay buffer (Hanks' solution buffered with 15 mM Hepes, pH 7.4, obtained from Sigma, St. Louis, Mo., U.S.A.) and recentrifuged at 300 rpm (21 g) for 10 min. The cells are then gently resuspended in assay buffer and examined using a hemacytometer for cell density and viability by trypan blue exclusion. Assays are performed using a Tomtec Quadra 96 pipeting robot, programmed to mix the cells gently after each addition. In 200 µL of assay buffer, $2 \times 10^5$ PTP expressing cells or mock infected cells are dispensed into each well of 96-well polypropylene plates and pre-incubated either with a test compound or DMSO vehicle (3 µL), for 15 min at 37° C. The pre-incubated cells are challenged with a final concentration of 10 mM pNPP (p-nitrophenyl phosphate, obtained from Sigma-Aldrich Canada Ltd., Oakville, Ontario) for 15 min, centrifuged at 4° C. and the amount of substrate hydrolysis is determined spectrophotometerically at $OD_{405}$.

Oral Glucose Tolerance Test

Oral glucose tolerance tests are done on conscious Zucker obese fa/fa rats or obese ob/ob mice (age 12 weeks or older). The animals are fasted for 16–18 hours before use for experiments. A test compound or a vehicle is given either intraperitoneally or orally 60 minutes before oral administration of a glucose solution at a dose of 2 g/kg body weight. Blood glucose levels are measured using a Medisense glucometer from tail bled samples taken at different time points before and after administration of glucose. A time curve of the blood glucose levels is generated and the area-under-the-curve (AUC) for 120 minutes is calculated (the time of glucose administration being time zero). Percent inhibition is determined using the AUC in the vehicle-control group as zero percent inhibition.

In separate studies, C57BL/6J mice are fed a high fat (35%) and high carbohydrate (36%) diet obtained from Bioserv (Frenchtown, N.J.) for 3 to 4 weeks, at which time the mice gained 50 –100% of the baseline body weight. Oral glucose tolerance tests are done in the same manner as described above.

EXAMPLES

The invention is further illustrated by the following examples, which are provided to illustrate the invention and are not to be construed as limiting the invention in any manner. In these examples, the following experimental methods and procedures were followed, unless stated otherwise:

(i) all operations were carried out at room or ambient temperature, that is, at a temperature in the range 18–25° C., (ii) evaporation of solvent was carried out using a rotary evaporator under reduced pressure (600–4000 pascals: 4.5–30 mm. Hg) with a bath temperature of up to 60° C., (iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta (δ) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), m.p. (melting point), L (liter(s)), mL (milliliters), g (gram (s)), mg (milligrams(s)), mol (moles), mmol (millimoles), eq (equivalent(s)).

Example 1

[2-bromo-4-(3-oxo-2,3-diphenylpropyl)phenyl](difluoro)methylphosphonic acid

Step 1 2-bromo-4-(bromomethyl)benzoic acid

2-Bromo-4-methylbenzoic acid (33.5 g, 156 mmol, 1 eq) and N-Bromosuccinimide (40.7 g, 233 mmol, 1.5 eq) were dissolved in refluxing 1,2-dichloroethane (600 ml) and a catalytic amount of AIBN was added. The mixture was left stirring under a lamp and under nitrogen for 1 hour. The solvent was removed and the mixture was partitioned between 600 ml of water and 600 ml EtOAc. The organic layer was washed twice with water (600 ml), washed once with brine (600 ml) and then dried with sodium sulfate. The solvent was removed and the crude mixture was triturated with 10% EtOAc/Hexane for 2 hours and 23.8 g (52%) of the title compound was obtained.

Step 2 2-bromo-4-(bromomethyl)phenyl)methanol

The compound of Step 1 (23.8 g, 81 mmol, 1 eq) was dissolved in THF under nitrogen at 0° C. A 1M borane solution in THF (242 ml, 242 mmol, 3 eq) was then added dropwise and the mixture was stirred at r.t. for 1 h. under nitrogen. The solution was cooled in an ice bath and 125 ml of methanol was then added slowly. The solvent was removed and the mixture partitioned between 400 ml of water and 400 ml of 20% THF/EtOAc. The aqueous layer was washed 3 times with 400 ml of 20% THF/EtOAc and the combined organic layer was dried with sodium sulfate. The solvent was removed and 19.7 g (87%) of the title compound was obtained.

Step 3 4-(bromomethyl)-2-bromobenzaldehyde

The compound of Step 2 (8 g, 29 mmol, 1 eq) was dissolved in 10% EtOH/EtOAc (300 ml) and 5 eq of $MnO_2$ (12.4 g, 142 mmol) was added every hour for 6 hours. The mixture was filtered through Celite and solvent was removed. 6.5 g (80%) of the title compound was obtained.

Step 4 di(tert-butyl) [2-bromo-4-(bromomethyl)phenyl](hydroxy)methylphosphonate

Di-tert-butyl phosphite (14.8 g, 76.3 mmol, 1.05 eq) was dissolved in 200 ml THF at −78° C. under nitrogen and 72 ml (1.05 eq) of 1.06M Lithium bis(trimethylsilyl)amide in THF was added over 30 min. The mixture was left stirring at −78° C. under nitrogen for 30 min and then added to a solution of the compound of Step 3 (20.2 g, 72.7 mmol, 1 eq) in 200 ml THF at −78° C. The solution was warmed to 0° C. and then poured into 400 ml of half saturated aqueous ammonium acetate. The layers were separated and the aqueous layer was washed with 400 ml isopropyl acetate. The organic layers were combined, dried with sodium sulfate and the solvent removed. The crude solid was then triturated with 15% EtOAc/hexane for 2 hours and 30.4 g (89%) of the title compound was obtained.

Step 5 di-(tert-butyl)-2-bromo-4-(bromomethyl) benzoylphosphonate

The compound of Step 4 was dissolved in acetone, and $MnO_2$ (40 equiv.) was added. The mixture was stirred vigorously for 2–7 hours, then filtered through Celite. The solvent was removed to provide the title compound. Alternatively, the title compound can be prepared by Swern oxidation of the compound of Step 4.

Step 6 di(tert-butyl)[2-bromo-4-(bromomethyl)phenyl](difluoro)methylphosphonate

To di(tert-butyl)-2-bromo-4-(bromomethyl) benzoylphosphonate (8.0 g, 17 mmol) was added 2-methyl-2-butene (8.0 mL). To the mixture at 0° C. was added diethylamino sulfur trifluoride (40 mL). After a period of 24 h, the reaction mixture was poured into 2.2 L of 1/1 ethylacetate-hexane, diisopropylethylamine (90 mL) and saturated $NaHCO_3$ (400 mL) at 0° C. The organic phase was separated, dried over $Na_2SO_4$, filtered and evaporated. The crude material was purified by flash chromatography (20% ethyl acetate in hexane) over silica gel previously washed with 20% ethyl acetate hexane containing 1% of $Et_3N$ to give 5.0 g of the title compound.

$^1$H NMR (400 MHz, $CDCl_3$) δ1.50 (18H, s), 4.40 (2H, s), 7.40 (1H, d), 7.60 (1H, d), 7.65 (1H, d).

Step 7 di(tert-butyl)[2-bromo-4-(3-oxo-2,3-diphenylpropyl)phenyl] (difluoro)methylphosphonate To a solution of deoxybenzoin (0.119 g, 0.607 mmol) in THF (3.3 mL) at −78° C., under nitrogen, was added a 1M solution of potassium tert-butoxide (0.672 mL, 0.672 mmol) followed by the bromide of Step 6 (0.300 g, 0.610 mmol). After a few minutes at room temperature, an aqueous solution of $NH_4OAc$ was added to the reaction mixture. To the resulting mixture EtOAc was then added. The organic phase was separated, dried over $Na_2SO_4$, filtered and evaporated under reduced pressure. The title compound was obtained after purification, by flash chromatography (0.300 g).

Step 8 2-bromo-4-(3-oxo-2,3-diphenylpropyl)phenyl](difluoro)methylphosphonic acid The compound of Step 7 (0.300 g) was dissolved in a 4/1 mixture of $HOAc/H_2O$. After a period of 18 h at room temperature, the solvents were evaporated under reduced pressure to give the title compound (0.260 g).

$^1$H NMR (400 MHz, $CD_3COD_3$) δ3.10 (1H, m), 3.55 (1H, m), 5.25 (1H, m), 7.20 –8.05 (13H, m).

Example 2

Difluoro(4-(3-oxo-2,3-diphenylpropyl)phenyl] methylphosphonic acid

Step 1 4-(bromomethyl)benzaldehyde

To a THF-toluene (2.4 L -0.24 L) solution of α bromo p tolunitrile (266.4 g, 1.36 mol) maintained at an internal temperature below 0° C. was added DIBAL-H in hexane (1.0 M) (1.49 L, 1.49 mol) over a period of 2 h. After a period of 1.5 h, the reaction mixture was transferred via canula to a 3N HCl solution (8 L) at 0° C. To the resulting suspension EtOAc (4 L) and THF (0.8 L) were added. After stirring, the organic phase was separated and evaporated to give a yellow solid. The solid was stirred, in 20% EtOAc in hexane (1.3 L) for 3 hours. After filtration and drying, the title compound was obtained (210 g).

Step 2 di(tert-butyl)[4-(bromomethyl)phenyl](hydroxy)methylphosphonate

To a solution of di-t-butylphosphite (125 g, 0.640 mol) in THF (2 L) was added LiHMDS (0.607 L, 0.643 mol) at −78° C. The lithium salt was transferred via canula to a −70° C. solution of the aldehyde of Step 1 (122 g, 0.612 mL) in THF (2 L). The resulting reaction mixture was warmed slowly to 0° C. After a period of 1 h at 0° C., aqueous $NH_4OAc$ (1.2 L) and isopropyl acetate (1 L) were added to the reaction mixture. The organic phase was separated, dried over $Na_2SO_4$, filtered and evaporated under reduced pressure. To the resulting solid was added 20% EtOAc in hexane (1 L) and the mixture stirred overnight. After filtration, the title compound was obtained as a white solid (184 g).

Step 3 di(tert-butyl) 4-(bromomethy)benzoylphosphonate

To the alcohol of Step 2 (184 g, 0.468 mol) in EtOAc (8.4 L) was added $MnO_2$ (407 g, 4.68 mol). After a period of 1 h, the reaction mixture was filtered over celite-silica gel. The solvent was evaporated and 10% EtOAc in Hexane (0.50 L) was added. The solid was filtered to provide 137 g of the title compound.

Step 4 di(tert-butyl)[4-(bromomethyl)phenyl](difluoro) methylphosphonate

To a toluene (250 mL) solution of 2-methyl-2-butene (17.8 g, 256 mmol) at 0° C. was added DAST (206 g, 1.28 mol). The ketone of Step 3 (50.0 g, 128 mmol) was then added portionwise. After a period of 18 h at room temperature, the reaction mixture was transferred dropwise to a mixture of saturated NaHCO$_3$ (1.2 L), EtOAc (1.2 L), and Et$_3$N (250 mL) at 0° C. The organic phase was separated, dried over Na$_2$SO$_4$, filtered and evaporated under reduced pressure. The compound was purified over silica gel with 20% EtOAc in hexane to provide 29.5 g of material.

Step 5 di(tert-butyl)difluoro[4-(3-oxo-2,3-diphenylpropyl) phenyl]methylphosphonate To a solution of deoxybenzoin (10 g, 51 mmol) and di(tert-butyl)[4-(bromomethyl)phenyl](difluoro) methylphosphonate (11.5 g, 28 mmol) in dry DMF (150 mL) at 0° C. was added the NaH (0.90 g, 30 mmol, 80% in oil). The ice bath was removed and the mixture was stirred at r.t. for 1 h. The reaction was then quenched with saturated NH$_4$Cl solution, and the product was extracted with Et$_2$O. The organic layer was washed with H$_2$O and brine, and was then dried (MgSO$_4$), filtered, and evaporated. The residue was stirred vigorously with 1:10 EtOAc:hexane (75 mL) for 2 h to give, after filtration, 8.8 g of white solid.

$^1$H NMR (acetone, d$_6$), 1.38 (s, 18H), 3.19–3.17 (m, 1H), 3.53–3.60 (m, 1H), 5.15 –5.61 (m, 1H), 7.14 –7.20 (m, 1H), 7.23 –7.29 (m, 2H), 7.29 –7.37 (m, 4H), 7.37 –7.43 (m, 4H), 7.48 –7.54 (m, 1H), 7.98–8.04 (m, 2H).

Step 6 difluoro[4-(3-oxo-2,3-diphenylpropyl)phenyl] methylphosphonic acid

To a solution of the phosphonate ester from Step 5 (0.16 g, 0.373 mmol) in HOAc (4 mL) was added H$_2$O (1 mL). After stirring overnight at r.t., the solvent was removed under vacuum and the residue was co-evaporated with toluene 2 times.

$^1$H NMR (400 MHz, CD$_3$COCD$_3$) δ3.10 (1H, m), 3.60 (1H, m), 5.20 (1H, m), 7.15 –8.05 (14H, m).

Example 3

4-[2-(Benzyloxy)-1-(methoxycarbonyl)-2-oxoethyl] phenyl(difluoro) methylphosphonic acid Step 1 1-benzyl 3-methyl 2-4-[(ditert-butoxyphosphoryl) (difluoro) methyl]phenylmalonate To a solution of benzyl methyl malonate (0.2 g) in DMF (8 mL), was added sequentially NaH (0.08 g, 60% in mineral oil), di(tert-butyl)[[4-(bromomethyl)phenyl](difluoro) methyl]phosphonate (0.83 g), and n-Bu$_4$NI(0.08 g). The reaction mixture was stirred at room temperature for 2.5 h, then quenched with 20 mL of saturated aqueous NH$_4$Cl solution and extracted with 50 mL of 1:1 hexane/EtOAc. The extract was dried over Na$_2$SO$_4$ and concentrated. The residue was purified by silica gel chromatography eluted with 2:1 hexane/EtOAc. First eluted was the title compound (0.2 g) as an oil, followed by 2,2-di {4-[(di-tert-butoxyphosphoryl)(difluoro)methyl]benzyl}malonic acid, benzyl methyl ester (0.3 g) as an oil.

$^1$H NMR (400 MHz, acetone-d$_6$) δ7.49 (2H, d), 7.25–7.40 (7H, m), 5.17 (1H, d), 5.11 (1H, d), 3.87 (1H, t), 3.64 (3H, s), 3.26 (2H, d), 1.44 (18H, s).

Step 2 4-[2-(Benzyloxy)-1-(methoxycarbonyl)-2-oxoethyl] phenyl (difluoro)methylphosphonic acid A solution of 1-benzyl 3-methyl 2-4-[(ditert-butoxyphosphoryl) (difluoro)methyl]phenylmalonate (Example 2, Step 4) (40 mg) in 1 mL of CH$_2$Cl$_2$, 3 mL of TFA and 0.2 mL of water was stirred for 2 h and then concentrated. The residue was dissolved in 3.5 mL of water and washed with 2×5mL of 1:1 hexane/ether and the aqueous solution was lyophilized to give 35 mg of the title compound as a syrup.

$^1$H NMR (400 MHz, methanol-d$_4$) δ7.52 (2H, d), 7.22–7.40 (7H, m), 5.16 (1H, d), 5.12 (2H, d), 3.88 (1H, t), 3.65 (3H, s), 3.25 (2H, d).

Example 4

2-Bromo-4-[2-phenyl-2-(3-phenyl-1,2,4-oxadiazol-5-yl) ethyl]phenyl (difluoro)methylphosphonic acid Step 1 benzene amidoxime A mixture of benzonitrile (5.2 g), hydroxlyamine hydrochloride (4.2 g) in EtOH (100 mL) was treated with 6 mL of aqueous 10 N NaOH solution. The resulting mixture was stirred overnight at room temperature and was then heated at 60° C. for 4 h. After cooling, the mixture was filtered and the filtrate was concentrated and co-evaporated with 2×100 mL of toluene to provide 8 g of the title compound as a white solid.

Step 2 5-benzyl-3-phenyl-1,2,4-oxadiazole

To a solution of phenylacetic acid (2.04 g) in 50 mL of DMF was added carbonyldiimidazole (2.7 g). The mixture was stirred for 20 min and then benzene amidoxime (2.04 g) was added. The resulting mixture was stirred for 20 min at r.t. and 18 h at 75 ° C. After cooling, the reaction mixture was poured in to 50 mL of water and extracted with 2×50 mL of 1:1 hexane/EtOAc. The extract was dried over MgSO4 and filtered. The filtrate was concentrated and the residue was purified by silica gel chromatography, eluting with 1:5 EtOAc/hexane to give 2 g of the title compound as a yellow syrup.

$^1$H NMR (400 MHz, acetone-d$_6$) δ8.05 (2H, m), 7.50–7.58 (3H, m), 7.43 (2H, d), 7.37 (2H, t), 7.32 (1H, t), 4.41 (2H, s).

Step 3 di(tert-butyl) [2-bromo-4-[2-phenyl-2-(3-phenyl-1,2,4-oxadiazol-5-yl)ethyl]phenyl(difluoro)methyl] phosphonate To a mixture of 5-benzyl-3-phenyl-1,2,4-oxadiazole (0.12 g), 18-crown-6 (0.02 g), in THF (5 mL) cooled at −60° C. was added dropwise a solution of KOtBu (0.5 mL, 1 M in THF). After stirring for 5 min, a solution of di(tert-butyl) [[2-bromo-4-(bromomethyl)phenyl](difluoro)methyl] phosphonate (Example 1, Step 6) (0.1 g in 0.7 mL of THF) was added and the resulting mixture was stirred for another 5 min at −60 ° C. and quenched with 3 mL of saturated NH$_4$Cl and 5 mL of water. The mixture was extracted with 30 mL of 2:1 hexane/EtOAc and the extract was dried over Na$_2$SO$_4$ and filtered. The filtrate was concentrated and the residue was purified by silica gel chromatography, eluting with 1:3 EtOAc/hexane containing 2 % Et$_3$N to give 0.13 g of the title compound as a syrup.

$^1$H NMR (400 MHz, acetone-d$_6$) δ7.65–7.70 (2H, m), 7.50–7.55 (1H, m), 7.35–7.47 (3H, m), 7.30–7.35 (4H, m), 7.22–7.27 (1H, m), 4.76 (1H, t), 3.77 (1H, dd), 3.47 (1H, dd), 1.38 (9H, s), 1.34 (9H, s).

Step 4 2-bromo-4-[2-phenyl-2-(3-phenyl-1,2,4-oxadiazol-5-yl)ethyl]phenyl(difluoro)methylphosphonic acid A solution of the product from Step 4 (0.13 g) in 3 mL of AcOH and 0.2 mL water was left at room temperature for 3 days and the co-evaporated with 3×3 ml of toluene to give 0.095 g of the title compound as a white solid.

$^1$H NMR (400 MHz, acetone-d$_6$) δ7.55–7.62 (3H, m), 7.45–7.55 (3H, m), 7.25–7.40 (7H, m), 4.73 (1H, dd), 3.78 (1H, dd), 3.46 (1H, dd).

Example 5

2-Bromo-4-[2-phenyl-2-(5-phenyl-1,2,4-oxadiazol-3-yl)ethyl]phenyl (difluoro)methylphosphonic acid Step 1 benzyl amidoxime Starting with benzylnitrile and hydroxyamine hydrochloride, the title compound was prepared as a white solid by using the same procedure described in Step 1 of Example 4.

Step 2 3-benzyl-5-phenyl-1,2,4-oxadiazole

Starting with benzyl amidoxime and benzoic acid, the title compound was prepared as a white solid by using the same procedure described in Step 2 of Example 4.

$^1$H NMR (400 MHz, acetone-$d_6$) δ8.10 (2H, d), 7.68 (1H, m), 7.62 (2H, m), 7.38 (2H, m), 7.33 (2H, t), 7.27 (1H, m), 4.17 (2H, s).

Step 3 di(tert-butyl) [2-bromo-4-[2-phenyl-2-(5-phenyl-1,2,4-oxadiazol-3-yl)ethyl]phenyl(difluoro)methyl]phosphonate Starting with 3-benzyl-5-phenyl-1,2,4-oxadiazole and di(tert-butyl)[[2-bromo-4-(bromomethyl)phenyl](difluoro)methyl]phosphonate, the title compound was prepared as an oil by using the same procedure described in Step 3 of Example 4.

$^1$H NMR (400 MHz, acetone-$d_6$) δ8.11 (2H, d), 7.57–7.70 (4H, m), 7.50 (2H, d), 7.45 (1H, d), 7.28–7.40 (3H. m), 7.25 (1H, m), 4.67 (1H, dd), 3.62 (1H, dd), 3.43 (1H, dd), 1.42 (9H, s), 1.38 (9H, s).

Step 4 2-bromo-4-[2-phenyl-2-(5-phenyl-1,2,4-oxadiazol-3-yl)ethyl]phenyl(difluoro)methylphosphonic acid Starting with di(tert-butyl) [2-bromo-4-[2-phenyl-2-(5-phenyl-1,2,4-oxadiazol-3-yl)ethyl]phenyl(difluoro)methyl]phosphonate, the title compound was prepared as a white solid by using the same procedure described in Step 4 of Example 4.

$^1$H NMR (400 MHz, acetone-$d_6$) δ8.12 (2H, d), 7.68 (1H, m), 7.57–7.66 (3H, m), 7.47–7.53 (3H, m), 7.30–7.38 (3H, m), 7.25 (1H, m). 4.66 (1H, dd), 3.64 (1H, dd), 3.42 (1H, dd).

Example 6

[4-(2-Benzotriazol-1-yl-2-m-tolylethyl)-phenyl]difluoromethylphosphonic acid

Step 1 1-(3-methylbenzyl)-1H-benzotriazole

To a solution of benzotriazole (3 g) in DMF (38 mL) at r.t. was added a solution of 10N NaOH (2.75 mL). After stirring for 25 min., 3-methylbenzyl bromide (3.9 mL) was added. The mixture was further stirred for 30 min, diluted with H$_2$O, and extracted with EtOAc. The EtOAc extract was washed with brine (2x), water, brine, and was then dried (MgSO$_4$) and concentrated. The residue was stirred in diethyl ether/hexane to give the title compound as a white solid.

$^1$H NMR (Acetone-$d_6$) δ8.02 (1H, d), 7.71 (1H, d), 7.49 (1H, m), 7.37 (1H, m), 7.24 –7.11 (4H, m) 5.92 (2H, s), 2.27 (3H, s).

Step 2 [4-(2-benzotriazol-1-yl-2-m-tolylethyl)-phenyl] difluoromethylphosphonic acid A solution of 1-(3-methylbenzyl)-1H-benzotriazole (1 g) in THF (25 mL) at –78° C. was placed under high vacuum for 5 min., then N$_2$ was introduced in the reaction vessel. A solution of 0.98M n-BuLi in hexanes (4.5 mL) was then added, and the solution turned deep blue immediately. After stirring for 5 min at –78° C., a solution of (4-bromomethylphenyl)-difluoromethylphosphonic acid di-tert-butyl ester (Example 2, Step 4) (1.85 g) in THF (3 mL) was added. The deep blue color disappeared. The mixture was then stirred at –78° C. for 10 min, then quenched with H$_2$O and extracted with EtOAc. The EtOAc extract was washed with brine, dried (MgSO$_4$) and concentrated. Chromatography over silica gel and elution with hexane:EtOAc (65:35), followed by stirring in diethyl ether provided 915 mg of the intermediate.

$^1$H NMR (Acetone-$d_6$) δ7.94 (1H, d), 7.76 (1H, d), 7.46–7.35 (9H, m), 7.30 (1H, t), 7.21 (1H, t), 7.10 (1H, d), 6.42(1H, t), 4.23 (1H, m), 4.06 (2H, m), 3.87 (1H, m), 2.28 (3H, s), 1.31 (18H, d).

Step 3 [4-(2-Benzotriazol-1-yl-2-m-tolylethyl)-phenyl] difluoromethy phosphonic acid.

The product from Step 2 was dissolved in HOAc (6 mL) and water (1.2 mL) and stirred at r.t overnight. After removal of solvents, the residue was stirred in diethyl ether to give 155 mg (55%) of the title compound as a white solid.

$^1$H NMR (Acetone-$d_6$) δ7.90 (1H, d), 7.74 (1H, d), 7.46–7.32 (7H, m), 7.24 (1H, t), 7.11(1H , d),6.47 (1H, m), 4.20 (1H, m), 3.85 (1H, dd), 2.28 (3H, s).

Example 7

{4-[2-Benzotriazol-1-yl-2-(4-fluorophenyl)-ethyl]-2-bromophenyl}difluoromethyl phosphonic acid Step 1 1-(4-fluorobenzyl)-1H-benzotriazole To a solution of benzotriazole (12 g) in DMF (150 mL) at r.t. was added a solution of 10N NaOH (11 mL). After stirring for 30 min., 4-fluorobenzyl bromide (3.9 mL) was added. The mixture was further stirred for 3 hrs, diluted with H$_2$O, and extracted with EtOAc. The EtOAc extract was washed water (2x), dried (MgSO$_4$) and concentrated. The residue was stirred in diethyl ether/hexane to afford the title compound as a white solid.

Step 2 {4-[2-benzotriazol-1-yl-2-(4-fluorophenyl)-ethyl]-2-bromophenyl}difluoromethylphosphonic acid.

A solution of 1-(4-fluorobenzyl)-1H-benzotriazole (91 mg) in THF (5 mL) at –78° C. was pumped under high vacuum for 5 min., then N$_2$ was introduced in the reaction vessel. A solution of 0.98M n-BuLi in hexanes (0.41 mL) was then added, and the solution turned deep blue immediately. After stirring for 5 min at –78° C., a solution of (2-bromo-4-bromomethylphenyl)difluoromethylphosphonic acid di-tert-butyl ester (Example 1, Step 6)(157 mg) in THF (1.5 mL) was added. The deep blue color disappeared. The mixture was then stirred at –78° C. for 15 min then quenched with H$_2$O and extracted with EtOAc. The EtOAc extract was washed with brine, dried (MgSO$_4$) and concentrated. Chromatography over silica gel and elution with hexane:EtOAc (65:35, 0.2% Et$_3$N), provided 85 mg of the intermediate.

$^1$H NMR (Acetone-$d_6$) δ7.96 (1H, d), 7.78 (1H, d), 7.71–7.32(7H, m), 7.13 (2H, t), 6.55 (1H, m), 4.19 (1H, m), 3.89(1H, m), 1.36 (18H, d).

Step 3 {4-[2-Benzotriazol-1-yl-2-(4-fluorophenyl)-ethyl]-2-bromophenyl}difluoromethyl phosphonic acid.

The above intermediate product was dissolved in HOAc (3 mL) and water (0.6 mL) and stirred at r.t overnight. After removal of solvent, the residue was stirred in diethyl ether to give the title compound as a white solid.

$^1$H NMR (Acetone-$d_6$) δ7.96 (1H, d), 7.75 (1H, d), 7.68 (1H, s), 7.61 (2H, m), 7.46 (2H, m), 7.35 (2H, t), 7.13 (2H, t,), 6.57 (1H, m), 4.18 (1H, m), 3.86 (1H, m).

Example 8

{4-[2-Benzotriazol-1-yl-2-(4-trifluoromethylphenyl)-ethyl]phenyl}difluoromethylphosphonic acid disodium salt Step 1 1-(3-trifluoromethylbenzyl)-1H-benzotriazole To a solution of benzotriazole (3 g) in DMF (38 mL) at r.t. was added a solution of 10N NaOH (2.75 mL). After stirring for 25 min., 3-trifluoromethylbenzyl bromide (4.39 mL) was added. The mixture was further stirred for 30 min., diluted with $H_2O$, and extracted with EtOAc. The EtOAc extract was washed brine (2×), water, brine, dried ($MgSO_4$) and concentrated. The residue was stirred in diethyl ether/hexane to afford 3.96 g of the title compound as a white solid.

Step 2 {4-[2-benzotriazol-1-yl-2-(3-trifluoromethylphenyl)-ethyl]phenyl}difluoromethylphosphonic acid disodium salt.

A solution of 1-(3-trifluoromethylbenzyl)-1H-benzotriazole (1 g) in THF (25 mL) at −78° C. was placed under high vacuum for 5 min., then $N_2$ was introduced in the reaction vessel. A solution of 0.98M n-BuLi in hexanes (3.67 mL) was added, and the solution turned deep blue immediately. After stirring for 5 min at −78° C., a solution of (4-bromomethylphenyl)difluoromethylphosphonic acid di-tert-butyl ester (Example 2, Step 4) (1.47 g) in THF (5 mL) was added. The deep blue color disappeared. The mixture was then stirred at −78° C. for 30 min then quenched with $H_2O$ and extracted with EtOAc. The EtOAc extract was washed with brine, dried ($MgSO_4$) and concentrated. Chromatography over silica gel and elution with hexane:EtOAc (65:35, 0.2% $Et_3N$), provided 1.9 g of the intermediate.

Step 3 {4-[2-Benzotriazol-1-yl-2-(3-trifluoromethylphenyl)-ethyl]phenyl}difluoromethylphosphonic acid disodium salt.

The above intermediate product (300 mg) was dissolved in HOAc (10 mL) and water (2 mL) and stirred at r.t overnight. After removal of solvent, the residue was chromatographed on reverse phase silica gel ($C_{18}$), using 30 to 50% $CH_3CN$ in water to afford the phosphonic acid (199 mg). The phosphonic acid was dissolved in water, sodium hydroxide 1N (0.8 ml) was added and the solution was lyophilized.

The residue was stirred in ethyl acetate, the suspension was centrifuged, the supernatant was discarded, more ethyl acetate was added. Vigorous mixing, followed by centrifugation and removal of the supernatant layer afforded the title compound after drying under high vacuum.

$^1$H NMR (Acetone-$d_6$) δ7.93 (1H, d), 7.80 (1H, s), 7.75 (1H, d), 7.69 (1H, d), 7.60 −7.50(4H, m), 7.46 (1H, t), 7.37 (1H, t), 7.20 (2H, d), 6.47 (1H, dd), 4.12 (1H, m), 3.75 (1H, m).

Example 9

(4-2-(1H-1,2,3-Benzotriazol-1-yl)-2-[4-(methyloxycarbonyl)phenyl]ethylphenyl)(difluoro) methylphosphonic acid Step 1 methyl 4-(1H-1,2,3-benzotriazol-1-ylmethyl) benzoate To a solution of benzotriazole (1.14 g, 9.6 mmol) in DMF (25 mL) at 0° C. was added methyl 4-bromomethylbenzoate (2.22, 9.6 mmol) and NaH (12.25 mmol, 60% in oil). After stirring for 2 h, the mixture was diluted with aqueous $NH_4Cl$, extracted with EtOAc. The EtOAc extract was washed $H_2O$ (3×), dried ($MgSO_4$) and concentrated. The residue was chromatographed to give 1.32 g (51%) of the title compound as a white powder.

Step 2 (4-2-(1H-1,2,3-benzotriazol-1-yl)-2-[4-(methyloxycarbonyl) phenyl]ethylphenyl)(difluoro) methylphosphonic acid di-tert-butyl ester To a solution of methyl 4-(1H-1,2,3-benzotriazol-1-ylmethyl)benzoate (804 mg, 3 mmol) and (4-bromomethylphenyl) difluoromethylphosphonic acid di-tert-butyl ester (Example 2, Step 4) (1.23 g, 3.0 mmol) in THF (20 mL) at −40° C. was added a solution of 1.0 M potassium tert-butoxide in THF (3.3 mL, 3.3 mmol). After stirring for 1 h at −40° C., aqueous $NH_4Cl$ was added, the mixture was extracted with EtOAc. The EtOAc extract was washed with brine, dried ($MgSO_4$) and concentrated. The residue was chromatographed to give 894 mg (50%) of the title compound as a white powder.

Step 3 (4-2-(1H-1-2,3-benzotriazol-1-yl)-2-[4-(methyloxycarbonyl) phenyl]ethylphenyl)(difluoro) methylphosphonic acid To a solution of the product obtained from Step 2 (48 mg, 0.079 mmol) in HOAc (1 mL) was added $H_2O$ (0.15 mL). The mixture was stirred at r.t. for 20 h. The solvent was evaporated to give the title compound.

$^1$H NMR (Acetone-$d_6$) δ3.83 (s, 3H), 3.86 (m, 1H), 4.20 (m, 1H), 6.55 (m, 1H), 7.34 (m, 6H), 7.63 (d, 2H), 7.72 (d, 1H), 7.95 (m, 3H).

Example 10

{4-[2-(1H-1,2,3-benzotriazol-1-yl)-2-(4-fluorophenyl)ethyl]phenyl}(difluoro) methylphosphonic acid The title compound was prepared as described in Steps 1 and 2 of Example 8, followed by Step 3 of Example 9.

$^1$H NMR (Acetone-$d_6$) δ7.91 (d, 1H), 7.74 (d, 1H), 7.60 (m, 2H), 7.50–7.30 (m, 6H), 7.11 (t, 2H), 6.52 (dd, 1H), 4.18 (dd, 1H), 3.86 (dd, 1H).

Example 11

{4-2-(1H-1,2,3-benzotriazol-1-yl)-2-phenylethyl] phenyl}(difluoro) methylphosphonic acid The title compound was prepared as described in Steps 1 and 2 of Example 8, followed by Step 3 of Example 9.

$^1$H NMR (Acetone-$d_6$) δ7.90 (d, 1H), 7.53 (d, 2H), 7.50–7.25 (m, 9H), 6.50 (dd, 1H), 4.20 (dd, 1H), 3.86 (dd, 1H).

Example 12

{[(2,2-dimethylpropanoyl)oxy]methyl}hydrogen [2-bromo-4-(3-oxo-2,3-diphenylpropyl)phenyl] (difluoro)methylphosphonate A mixture of [-2-bromo-4-(3-oxo-2,3-diphenyl propyl) phenyl](difluoro)methyl phosphonic acid (Example 1) (2.00 g, 4.0 mmol), chloromethyl pivalate (6.0 mL) and $Cs_2CO_3$ (2.50 g) in $CH_3CN$ (60 mL) was refluxed for 18 h. The reaction mixture was partitioned between saturated $NH_4Cl$ and EtOAc. The organic phase was separated, dried over $Na_2SO_4$ and evaporated underreduced pressure. The title compound was purified by flash chromatography (1.4 g)

$^1$H NMR (400 MHz, acetone $d_6$) δ1.15 (9H, s), 3.05 (1H, m), 3.50 (1H, m), 5.10 (1H, t), 5.45 (2H, AB), 7.15 (13H, m).

Example 13

Bis{[(2,2-dimethylpropanoyl)oxy]methyl}[2-bromo-4-(3-oxo-2,3-diphenylpropyl) phenyl](difluoro) methylphosphonate To disilver [2-bromo-4-(3-oxo-2,3-diphenyl propyl) phenyl](difluoro, methylphosphonate (prepared according to the procedure in Eur. J. of Pharm. Sci. 4, 49–59 (1996)) (2.65 g, 3.71 mmol) in $CH_3CN$ (15 mL) was added iodomethyl pivalate (2.71 g, 11.15 mmol). The reaction mixture was stirred at room temperature overnight, and was then evaporated to dryness. The residue was dissolved in dichloromethane and flash chromatography 1.6 g.

$^1$H NMR (300 MHz, acetone-d$_6$) δ8.02 (2H, d), 7.62 (1H, s), 7.12–7.52 (10H, m), 5.7 (4H, m), 5.2 (1H, t), 3.52 (1H, m), 3.12 (1H, m), 1.18 (18H, s).

Example 14

1-{[[[2-bromo-4-(3-oxo-2,3-diphenylpropyl)phenyl](difluoro)methyl](hydroxy)phosphoryl]oxy}-2-methylpropyl propionate Step 1 1-Chloro-2-methylpropyl propionate To a flask containing ZnCl$_2$ (0.57 g) at 0° C. was added dropwise propionyl chloride (32.0 g) followed by isobutyraldehyde (25.0 g) over 30 min. After a period of 2 h at room temperature, saturated NaHCO$_3$ solution was added to the reaction mixture. The mixture was then extracted with EtOAc, dried over NaSO$_4$, filtered and evaporated under reduced pressure. The title compound was distilled using a water pump aspirator Step 2 1-{[[[2-bromo-4-(3-oxo-2,3-diphenylpropyl)phenyl](difluoro)methyl](hydroxy)phosphoryl]oxy}-2-methylpropyl propionate The title compound was prepared as described in Example 12.1 $^1$H NMR (400 MHz, acetone-6) δ0.90 to 1.1 (m, 9H), 1.95 (m, 1H), 2.30 (q, 2H), 3.05 (m, 1H), 3.50 (m, 1H), 5.05 (m, 1H), 6.40 (m, 1H), 7.15 to 8.00 (m, 13H).

Example 15

[1-(isobutyryloxy)ethyl]hydrogen[2-bromo-4-(3-oxo-2,3-diphenylpropyl)phenyl](difluoro)methylphosphonate Step 1 1-chloroethyl-2-methylpropanoate The literature procedure (Synth. Comm. 2739 (1995)) was modified as follows. To a flask containing dry ZnCl$_2$ (1.36 g, 10 mmol) under N$_2$ at 0° C. was added 2-methylpropanoyl chloride (52.4 mL, 0.5 mol). After stirring for 5 min at 0° C., acetaldehyde (28 mL, 0.5 mol) was added dropwise over a period of 1 h. The mixture was stirred a further 1.5 h, at which point it was partitioned between Et$_2$O and saturated NaHCO$_3$ solution. The organic phase was dried (MgSO$_4$), filtered, and evaporated to give a brown oil. A portion of this was distilled under water aspirator vacuum to give a colorless oil bp. 48–50° C.

Step 2 1-iodoethyl-2-methylpropanoate

To a solution of the chloro compound from Step 1 (2.6 g, 17.3 mmol) in CH$_3$CN (20 mL) at r.t. was added NaI (2.85 g, 19 mmol). The flask was covered with Al foil and the reaction was stirred ON at r.t. The orange suspension was filtered and the filtrate was evaporated to dryness. The crude product was dissolved in Et$_2$O/H$_2$O and the organic phase was washed with aqueous sodium metabisulfite and brine. After drying (MgSO$_4$), filtering, and removal of solvent, a pale brown oil (1.92 g) was obtained.

Step 3 1-{[(2-bromo-4-(3-oxo-2,3-diphenylpropyl)phenyl](difluoro)methyl](hydroxy)phosphoryl]oxy}ethyl 2-methylpropanoate To a solution of the silver salt from Example 13 (50 mg, 0.07 mmol) in CH$_3$CN (1.0 mL) at r.t. was added 1-iodoethyl-2-methylpropanoate (51 mg, 0.21 mmol). After 2.5 h at r.t. the solvent was evaporated and the residue was applied directly to a flash column as a suspension in CH$_2$Cl$_2$. Elution with 1:10 MeOH:CH$_2$Cl$_2$ afforded the title compound as a tan colored foam (26 mg). MS–ESI M$^{-1}$=608.8

Example 16

Bis[(isobutyryloxy)methyl][2-bromo-4-(3-oxo-2,3-diphenylpropyl)phenyl](difluoro)methylphosphonate Step 1

To a solution of (2-bromo-4-(3-oxo-2,3-diphenylpropyl)phenyl](difluoro) methylphosphonic acid (0.5 g, 9.27 mmol) in ethanol (1 mL) was added a solution of silver trifluoroacetate (0.4 g, 1.81 mmol) in ethanol (1 mL) at room temperature. The reaction mixture was stirred for 1 hour. Then, the suspension thus obtained was evaporated to dryness. The residue was co-distilled with toluene followed by acetonitrile, then the solid was pumped under high vacuum overnight.

Step 2

To disilver [2-bromo-4-(3-oxo-2,3 diphenylpropyl)phenyl](difluoro) methylphosphonate (0.7 g, 9.27 mmol) in acetonitrile (5 mL) was added iodomethyl 2-methylpropanoate (Synth. Comm. 25 (18), 2739–49 1995) at r.t. The reaction mixture was stirred overnight. The mixture was evaporated to dryness and redissolved in dichloromethane. Flash chromatography (30% EtOAc/hexane) then gave the title compound (0.15 g).

$^1$H NMR (300 MHz, acetone-d$_6$) δ8.02 (2H, d), 7.6 (1H, s), 7.12–7.55 (10H, m), 5.6 –5.75 (4H, m), 5.22 (1H, t), 3.55 (1H, m), 3.15 (1H, m), 2.6 (2H, m), 1.14 (12H,d).

Example 17

[(isobutyryloxy)methyl]hydrogen [2-bromo-4-(3-oxo-2,3-diphenylpropyl)phenyl](difluoro)methylphosphonate The title compound was obtained from further elution (with 10% MeOH/CH2CL2) of the chromatography of Example 16.

$^1$H NMR (300 MHz, acetone-d$_6$) δ8.02 (2H, d), 7.11–7.62 (11H, m), 5.55 (4H, m), 5.19 (1H, m), 3.50 (1H, m), 3.00 (1H, m), 2.40 (2H, m), 1.0 (6H, m).

Example 18

Bis {[(isopropoxycarbonyl)oxy]methyl}[2-bromo-4-(3-oxo-2,3-diphenylpropyl) phenyl](difluoro)methylphosphonate To disilver [2-bromo-4-(3-oxo-2,3-diphenylpropyl)phenyl](difluoro) methyl phosphonate (see Example 13) (0.9 g, 1.7 mmol) in CH$_3$CN (10 mL) was added iodomethyl isopropyl carbonate (Antiviral chemistry and chemotherapy 1997 8(6), 557) at r.t. The reaction mixture was stirred overnight. The reaction mixture was evaporated and redissolved in dichloromethane and flash chromatography (30% EtOAc/hexane) gave the title compound 0.07 g.

$^1$H NMR (300 MHz, acetone-d$_6$) δ8.0 (2H, d), 7.6 (1H, s), 7.15–7.55 (10H, m), 5.72 (4H, m), 5.22 (1H, t), 5.10 (2H, m), 3.55 (1H, m), 3.15 (1H, m), 1.30 (12H, d).

Example 19

[(isopropoxycarbonyl)oxy]methyl hydrogen [2-bromo-4-(3-oxo-2,3-diphenyl)phenyl](difluoro) methylphosphate From the previous flash chromatography (Example 18), further elution with 10% MeOH/CH$_2$Cl$_2$ gave the title compound 0.168 g.

$^1$H (300 MHz, methanol-d$_4$) δ7.95 (2H, d), 7.1–7.55 (11H, m), 5.4 (2H, m), 5.02 (1H, t), 3.45 (1H, m), 3.02 (1H, m), 1.25 (6H, d).

Example 20

Dibenzyl[2-bromo-4-(3-oxo-2,3-diphenylpropyl) phenyl](difluoro)methylphosphonate To disilver [2-bromo-4-(3-oxo-2,3- diphenylpropyl) phenyl](difluoro) methylphosphonate (see Example 13) (0.4 g, 0.56 mmol) in CH$_3$CN (4 mL) was added benzyl bromide 0.33 g, 1.9 mmole) at room temperature. The reaction mixture was stirred overnight, and was then evaporated to dryness. The residue was redissolved in dichlomethane and flash chromatography (30% EtOAc/hexane) gave the title compound 0.09 g.

$^1$H NMR(300 MHz, acetone-d$_6$) δ8.02 (2H, d), 7.6 (1H, s), 7.1–7.52 (20H, m), 5.2 (1H, t), 4.95–5.15 (4H, m), 3.52 (1H, m), 3.12 (1H, m).

Example 21

Benzyl hydrogen [2-bromo-4-(3-oxo-2,3-diphenylpropyl)phenyl](difluoro) methylphosphonate Further elution of the flash chromatography of Example 21 with 10% MeOH/CH$_2$Cl$_2$ afforded the title compound 0.09 g.

$^1$H NMR(300 MHz, acetone-d$_6$) δ7.98 (2H, d), 7.0–7.5 (16H, m), 4.98–5.15 (3H, m), 3.35 (1H, m), 2.85 (1H, m).

Example 22

[2-bromo-4-(3-oxo-2-phenylbutyl)phenyl](difluoro) methylphosphonic acid

Step 1 di(tert-butyl) [2-bromo-4-(3-oxo-2-phenylbutyl) phenyl](difluoro)methylphosphonate To a degassed solution of 1-phenylacetone (100 mg, 0.75 mmol) and di(tert-butyl)-2-bromo-4-(bromomethyl)phenyl (difluoro)methyl phosphonate (Example 1 Step 6) (367 mg, 0.75 mmol) in DMF (3 mL) at 0° C. was added NaH (80% in oil, 25 mg, 0.82 mmol). After 10 min at 0° C., the ice bath was removed and the reaction was stirred at r.t. for 30 min. The reaction was quenched with saturated NH$_4$Oac solution and the product was extracted with Et$_2$O. The organic layer was washed with H$_2$O and brine, and was then dried (MgSO$_4$), filtered, and evaporated. The residue was purified by flash chromatography (1:5 followed by 1:2 EtOAc:hexane) to give a colorless oil (230 mg).

Step 2 [2-bromo-4-(3-oxo-2-phenylbutyl)phenyl] (difluoro)methylphosphonic acid

The title compound was prepared from the product of Step 1 according to the procedure of Example 1 Step 8.

$^1$H NMR (CD$_3$COCD$_3$) δ2.00 (3H, s), 2.90–2.97 (1H, m), 3.34–3.52 (1H, m), 4.20 –4.26 (1H, m), 7.19–7.24 (1H, m), 7.24–7.30 (3H, m), 7.30–7.36 (2H, m), 7.46–7.52 (2H, m).

Example 23

{2-bromo-4-[3-oxo-2-phenyl-3-(1,3-thiazol-2-yl) propyl]phenyl}(difluoro) methylphosphonic acid Step 1 1,3-thiazol-2-yl[(trimethylsilyl)oxy]acetonitrile To a solution of 1,3-thiazole-2-carbaldehyde (1.0 g, 8.8 mmol) and ZnI$_2$ (10 mg) in CH$_2$Cl$_2$ (10 mL) was added TMSCN (1.65 mL, 12.4 mmol). After stirring ON at r.t., the solvent was removed to give the desired compound as a syrup (1.9 g).

Step 2 2-phenyl-1-(1,3-thiazol-2-yl)ethanone

To a solution of the product from Step 1 (0.4 g, 1.9 mmol) in degassed THF (4 mL) at −78° C. was added LHMDs.

After stirring at −78° C. for 15 min, benzyl bromide (0.27 mL, 2.3 mmol) was added, and stirring was continued at −78° C. for 15 min, followed by 1 h at r.t. The reaction was then quenched by the addition of saturated NH$_4$Cl solution, and the product was extracted with EtOAc. The organic layer was washed with H$_2$O and brine, and was then dried (MgSO$_4$), filtered, and evaporated. The residue was purified by flash chromatography (1:10 EtOAc:hexane) to give 0.16 g of the product.

Step 3 di(tert-butyl) {2-bromo-4-[3-oxo-2-phenyl-3-(1,3-thiazol-2-yl)propyl]phenyl}(difluoro)methylphosphonate To a degassed solution of the product from Step 2 (0.16 g, 0.79 mmol) and di(tert-butyl) [2-bromo-4-(bromomethyl) phenyl](difluoro)methylphosphonate (Example 1, Step 6) (387 mg, 0.79 mmol) in DMF (4 mL) at 0° C. was added NaH (80% in oil, 26 mg, 0.86 mmol). The ice bath was removed and the mixture was stirred at r.t. for 30 min. Saturated NH$_4$Oac solution was then added, and the product was extracted with Et$_2$O. The organic layer was washed with H$_2$O and brine, and was then dried (MgSO$_4$), filtered, and evaporated. After flash chromatography with 1:2 EtOAc: hexane, the product was obtained as a beige foam. (0.27 g).

Step 4 {2-bromo-4-[3-oxo-2-phenyl-3-(1,3-thiazol-2-yl) propyl]phenyl}(difluoro) methylphosphonic acid The title compound was obtained from the product of Step 2 following the procedure described in Example 1 Step 8.

$^1$H NMR (CD$_3$COCD$_3$) δ3.15–3.26 (1H, m), 3.55–3.66 (1H, m), 5.42–5.50 (1H, m) 7.16–7.46 (6H, m), 7.46–7.56 (1H, m), 7.56–7.63 (1H, m), 7.97–8.07 (2H, m).

Example 24

{2-bromo-4-[2-(4-methoxy-1,3-thiazol-2-yl)-3-oxo-3-phenylpropyl)phenyl}(difluoro) methylphosphonic acid Step 1 2-(4-methoxy-1,3-thiazol-2-yl)-1-phenylethanone To a suspension of 2-(4-hydroxy-1,3-thiazol-2-yl)-1-phenylethan-1-one (0.5 g, 2.3 mmol) in acetone (10 mL) at r.t. was added MeI (0.17 mL, 2.7 mmol), followed by K$_2$CO$_3$ (315 mg, 2.3 mmol). After stirring ON at r.t., the solvent was removed and the residue was taken up in Et$_2$O/H$_2$O. The organic layer was dried (MgSO$_4$), filtered, and evaporated to yield o.43 g of the title compound.

Step 2 di(tert-butyl) {2-bromo-4-[2-(4-methoxy-1,3-thiazol-2-yl)-3-oxo-3-phenylpropyl]phenyl}(difluoro) methylphosphonate To a degassed solution of the product from Step 1 (0.15 g, 0.61 mmol) in THF (3 mL) at −78° C. was added KOtBu. After 10 min, a solution of the product from Example 1 Step 6 (0.3 g, 0.61 mmol) in THf (2 mL) was added. The reaction was stirred at −78° C. for 30 min, followed by 30 min at r.t. Saturated NH$_4$Cl solution was then added, and the product was extracted with EtOAc. The organic layer was washed with H$_2$O and brine, and was then dried (MgSO$_4$), filtered, and evaporated. Flash chromatography (1:5 followed by 1:2 EtOAc:hexane) gave the product as an orange-colored syrup (45 mg).

Step 3 {2-bromo-4-[2-(4-methoxy-1,3-thiazol-2-yl)-3-oxo-3-phenylpropyl) phenyl}(difluoro) methylphosphonic acid The title compound was prepared from the product of Step 2 in the same manner as described in Example 1 Step 8.

$^1$H NMR (CD$_3$COCD$_3$) δ3.05–3.15 (1H, m), 3.22 (3H, s), 3.51–3.59 (1H, m), 4.40 –4.47 (1H, m), 6.92 (1H, s), 7.43–7.51 (3H, m), 7.51–7.58 (1H, m), 7.62–7.68 (1H, m), 7.68–7.73 (1H, m), 7.98–8.04 (2H, m).

What is claimed is:

1. A compound represented by formula I:

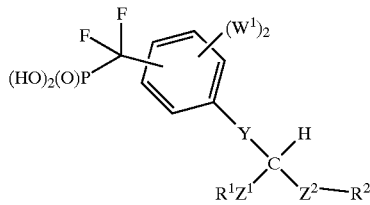

or a pharmaceutically acceptable salt thereof, wherein:

$R^1$ and $R^2$ are selected from the group consisting of: $C_{1-10}$alkyl$(R^a)_{0-7}$, $C_{2-10}$alkenyl$(R^a)_{0-7}$, Aryl$(R^a)_{0-3}$ and Het$(R^a)_{0-3}$;

wherein, each $R^a$ independently represents a member selected from the group consisting of: Aryl, OH, CN, halogen, $CO_2H$, $CO_2C_{1-6}$alkyl, $OC_{1-6}$alkyl, $C_{1-6}$alkyl, $OC_{1-10}$alkyleneCO$_2$H, OAryl, $C_{0-6}$alkyleneSO$_3$H, $C_{0-6}$alkyleneCO$_2$H, $C_{0-6}$alkyleneCO$_2$C$_{1-6}$alkyl, $C_{0-6}$alkyleneCO$_2$C$_{2-6}$alkenyl, $C_{0-6}$alkyleneC(O)C$_{1-6}$alkyl, C(O)NR$_3$·R$_4$·, NR$_3$·R$_4$·, $C_{1-6}$haloalkyl, $OC_{1-6}$haloalkyl, $S(O)_y C_{1-6}$alkyl, $S(O)_y NR^{3'}R^{4'}$, and Het, wherein y is 0, 1, or 2, wherein Het, Aryl, alkyl, and alkenyl in $R^a$ are optionally substituted with 1–3 substituents independently selected from halogen, $C_{1-6}$alkyl, $C_{1-6}$haloalkyl, $CO_2H$, $CO_2C_{1-6}$alkyl, $OC_{1-10}$alkyl, OH, Het and Aryl, where said Het and Aryl are optionally substituted with 1–2 substituents independently selected from halogen, $C_{1-3}$alkyl, $OC_{1-3}$alkyl, $CF_3$, and $OCF_3$;

Aryl is a 6–14 membered carbocyclic aromatic ring system comprising 1–3 phenyl rings, wherein said rings are fused together so that adjacent rings share a common side when there is more than one aromatic ring;

Het represents a 5–10 membered aromatic ring system comprising one ring or two fused rings, 1–4 heteroatoms, 0–4 of which are N atoms and 0–2 of which are O or $S(O)_y$ wherein y is 0–2, and 0–2 carbonyl groups;

y, $Z^1$ and $Z^2$ each independently represents $-(CR^3R^4)_a-X-(CR^3R^4)_b-$ wherein a and b are either 0 or 1, such that the sum of a and b equals 0, 1 or 2;

X represents a bond, O, $S(O)_y$, $NR^{3'}$, C(O), OC(O), C(O)O, C(O)NR$^{3'}$, NR$^{3'}$C(O) or —CH=CH—, where y is as previously defined;

$R^3$ and $R^4$ are independently H, halo, $C_{1-3}$alkyl, or $C_{1-3}$haloalkyl;

each $R^{3'}$ is independently selected from the group consisting of: H, $C_{1-6}$alkyl, $C_{1-6}$haloalkyl, OH, C(O)C$_{1-6}$alkyl, C(O)Aryl, C(O)Het, C(O)C$_{1-6}$ haloalkyl, Aryl and Het;

each $R^{4'}$ is independently selected from the group consisting of: H, $C_{1-6}$alkyl, $C_{1-6}$haloalkyl, Aryl and Het; and each $W^1$ is independently selected from the group consisting of: H, OH, CN, halogen, $OC_{1-6}$alkyl$(R^a)_{0-3}$, $S(O)_y C_{1-6}$alkyl$(R^a)_{0-3}$, with y equal to 0–2, $S(O)_3H$, $C_{1-6}$alkyl$(R^a)_{0-3}$, $C_{1-6}$haloalkyl$(R^a)_{0-3}$, $CO_2H$, $CO_2C_{1-6}$alkyl$(R^a)_{0-3}$, $CO_2C_{1-6}$haloalkyl$(R^a)_{0-3}$, $CO_2C_{2-6}$alkenyl$(R^a)_{0-3}$, $C(O)C_{1-6}$alkyl$(R^a)_{0-3}$, C(O)NR$^{3'}$R$^{4'}$, $S(O)_y NR^{3'}R^{4'}$, NR$^{3'}$R$^{4'}$, Aryl and Het, wherein R$^{3'}$ and R$^{4'}$ are as defined above, and wherein Aryl and Het may be unsubstituted or are optionally substituted with 1–3 substituents independently selected from the group consisting of halogen, $C_{1-6}$alkyl, $C_{1-6}$haloalkyl, $CO_2H$, $CO_2C_{1-6}$alkyl, $OC_{1-6}$alkyl, $OC_{1-6}$haloalkyl, and OH; or the two $W^1$ groups are on adjacent positions of the aromatic ring and are taken in combination to represent a fused phenyl ring.

2. A compound in accordance with claim 1 wherein each $W^1$ represents H or halogen.

3. A compound in accordance with claim 2, wherein one $W^1$ group represents H and the other $W^1$ group represents a halogen in the position adjacent to —CF$_2$P(O)(OH)$_2$ on the aromatic ring.

4. A compound in accordance with claim 1 wherein each Het is selected from the group consisting of: pyridinyl, 1H-1,2,3-benzotriazolyl, 1,2,4-oxadiazolyl and 1,3-thiazolyl.

5. A compound in accordance with claim 1 wherein Y is —CH$_2$—.

6. A compound in accordance with claim 1 wherein $Z^1$ and $Z^2$ are each independently selected from the group consisting of: CH2, —C(O)—, and a direct bond.

7. A compound in accordance with claim 1, wherein $R^1$ and $R^2$ are each independently selected from Aryl$(R^a)_{0-3}$ and Het$(R^a)_{0-3}$.

8. A compound having formula I, wherein $R_1$ and $R_2$ are each independently selected from the group consisting of (a) (CH$_2$)$_{0-3}$phenyl, which is optionally mono, di-, or trisubstituted, wherein the substituents are selected from the group consisting of:
  (1) halo,
  (2) $C_{1-6}$alkoxy,
  (3) $C_{1-6}$alkylthio,
  (4) $C_{1-6}$alkyl,
  (5) $C_{1-6}$fluoroalkyl,
  (6) —CO$_2$H,
  (7) —CO$_2$—C$_{1-4}$alkyl,
  (8) —CO$_2$C$_{1-4}$fluoroalkyl,
  (9) heteroaryl, which is optionally mono, di-, or trisubstituted, wherein the substituents are independently selected from the group consisting of halogen, $C_{1-6}$alkoxy, $C_{1-6}$alkylthio, $C_1$–$C_6$fluoroalkyl, $C_{1-6}$alkyl, —CO$_2$H, —CO$_2$C$_{1-4}$alkyl, —CO$_2$C$_{1-4}$fluoroalkyl, phenyl, and heteroaryl, wherein the phenyl and heteroaryl are optionally substituted with 1–2 groups independently selected from the groups listed in (a)(1)–(a)(8) of this claim, and
  (10) phenyl, which is optionally substituted with 1–2 substituents independently selected from the group consisting of halogen, $C_{1-6}$alkoxy, $C_{1-6}$alkylthio, $C_{1-6}$alkyl, $C_{1-6}$fluoroalkyl, —CO$_2$H, —CO$_2$C$_{1-4}$alkyl, —CO$_2$C$_{1-4}$fluoroalkyl, phenyl and heteroaryl, wherein the phenyl and heteroaryl are optionally substituted with 1–2 groups independently selected from the groups listed in (a)(1)–(a)(8) of this claim, and (b) heteroaryl, which is optionally mono-, di- or trisubstituted, wherein the substituents are independently selected from the group consisting of:
  (1) halo,
  (2) $C_{1-6}$alkoxy,
  (3) $C_{1-6}$alkylthio,
  (4) $C_{1-6}$fluoroalkyl,
  (5) $C_{1-6}$alkyl,
  (6) —CO$_2$H,
  (7) —CO$_2$—C$_{1-4}$alkyl,
  (8) —CO$_2$C$_{1-4}$fluoroalkyl, (9) phenyl, which is optionally substituted with 1–2 substituents independently selected from the group consisting of halogen, $C_{1-6}$alkoxy, $C_{1-6}$alkylthio, $C_{1-6}$alkyl, $C_{1-6}$fluoroalkyl, $CO_2H$, —$CO_2C_{1-4}$alkyl, —$CO_2C_{1-4}$fluoroalkyl, phenyl and heteroaryl, wherein the phenyl and heteroaryl are optionally substituted with 1–2 groups independently selected from the groups listed in (a)(1)–(a)(8) of this claim, and

(10) heteroaryl, which is optionally substituted with 1–2 substituents independently selected from the group consisting of halogen, $C_{1-6}$alkoxy, $C_{1-6}$alkylthio, $C_{1-6}$alkyl, $C_{1-6}$fluoroalkyl, phenyl and heteroaryl, wherein the phenyl and heteroaryl are optionally substituted with 1–2 groups independently selected from the groups listed in (a)(1)–(a)(8) of this claim, wherein each $W^1$ is independently selected from the group consisting of: halogen, $C_{1-6}$alkyl, and $C_{1-6}$fluoroalkyl;

Y is —$CH_2$—; and $Z^1$, and $Z^2$ are independently selected from the group consisting of $CH_2$, $CH_2CH_2$, C(O), C(O)$CH_2$, $CH_2$C(O)—, —OC(O)—, C(O)O, and a direct bond.

9. A compound in accordance with claim 8, wherein $R^1$ and $R^2$ are each independently selected from the group consisting of —($CH_2$)phenyl, phenyl, 1,2,4-oxadiazolyl, pyridinyl, and 1H-1,2,3-benzotriazolyl, each of which is optionally substituted with 1–3 substituents independently selected from halogen, $C_{1-3}$alkyl, $CF_3$, phenyl and 1,2,4-oxadiazolyl, wherein phenyl and 1,2,4-oxadiazolyl are optionally substituted with 1–3 substituents independently selected from $C_{1-3}$alkyl, $CF_3$, phenyl, and 1,2,4-oxadiazolyl, $Z^1$ and $Z^2$ are each CO, —OC(O)—, —C(O)O—, or a direct bond, Y is $CH_2$, and each $W^1$ is independently selected from the group consisting of hydrogen, halogen, and $C_{1-3}$alkyl, and is in a position on the aromatic ring adjacent to the —$CF_2P(O)(OH)_2$ group.

10. A compound having the formula shown below, or a pharmaceutically acceptable salt or prodrug thereof:

TABLE 1

Structures of Examples

| | Example | Method |
|---|---|---|
| [structure: H₂O₃P-CF₂- attached to benzene ring with Br substituent, connected via CH₂ to CH(Ph)C(O)Ph] | 1 | A + C |
| [structure: H₂O₃P-CF₂- attached to benzene ring, connected via CH₂ to CH(Ph)C(O)Ph] | 2 | B + C |
| [structure: F₂(PO₃H₂)C- attached to benzene ring, connected via CH₂ to CH(C(O)OMe)(C(O)OBn)] | 3 | B + D |

TABLE 1-continued

Structures of Examples

| Example | Method |
|---------|--------|
| 4 | A + I + D |
| 5 | A + H + D |
| 6 | B + D |
| 7 | A + D |

TABLE 1-continued

Structures of Examples

| Example | Method |
|---|---|
| 8 | B + D |
| 9 | B + D |
| 10 | B + D |
| 11 | B + D |
| 12 | A + C + F |

TABLE 1-continued

Structures of Examples

| Example | Method |
|---|---|
| 13 | A + C + G |
| 14 | A + C + F |
| 15 | A + C + G |
| 16 | A + C + G |

TABLE 1-continued

Structures of Examples

| Example | Method |
|---------|--------|
| 17 | A + C + G |
| 18 | A + C + G |
| 19 | A + C + G |
| 20 | A + C + G |
| 21 | A + C + G |
| 22 | A + D |

TABLE 1-continued

Structures of Examples

| | Example | Method |
|---|---|---|
| (structure) | 23 | A + D |
| (structure) | 24 | A + D |

TABLE 2

TABLE 2-continued

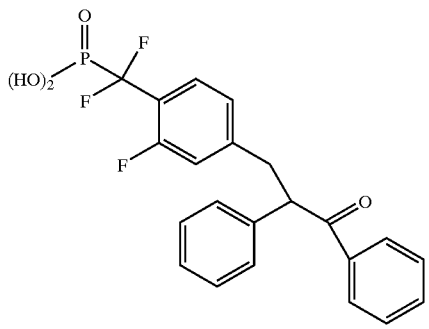

11. A compound as named below, or a pharmaceutically acceptable salt or prodrug thereof:

Example 1: [2-bromo-4-(3-oxo-2,3-diphenylpropyl) phenyl](difluoro)methylphosphonic acid;

Example 2: Difluoro(4-(3-oxo-2,3-diphenylpropyl) phenyl]methylphosphonic acid;

Example 3: 4-[2-(Benzyloxy)-1-(methoxycarbonyl)-2-oxoethyl]phenyl(difluoro) methylphosphonic acid;

Example 4: 2-Bromo-4-[2-phenyl-2-(3-phenyl-1,2,4-oxadiazol-5-yl) ethyl] phenyl (difluoro) methylphosphonic acid;

Example 5: 2-Bromo-4-[2-phenyl-2-(5-phenyl-1,2,4-oxadiazol-3-yl)ethyl]phenyl (difluoro) methylphosphonic acid;

Example 6: [4-(2-Benzotriazol-1-yl-2-m-tolylethyl)-phenyl]difluoromethylphosphonic acid;

Example 7: {4-[2-Benzotriazol-1-yl-2-(4-fluorophenyl)-ethyl]-2-bromophenyl} difluoromethyl phosphonic acid;

Example 8: {4-[2-Benzotriazol-1-yl-2-(4-trifluoromethylphenyl)-ethyl] phenyl} difluoromethylphosphonic acid disodium salt;

Example 9: (4-2-(1H-1,2,3-Benzotriazol-1-yl)-2-[4-(methyloxycarbonyl)phenyl] ethylphenyl)(difluoro) methylphosphonic acid;

Example 10: {4-[2-(1H-1,2,3-benzotriazol-1-yl)-2-(4-fluorophenyl)ethyl]phenyl} (difluoro) methylphosphonic acid;

Example 11: {4-[2-(1H-1,2,3-benzotriazol-1-yl)-2-phenylethyl]phenyl}(difluoro) methylphosphonic acid;

Example 12: {[(2,2-dimethylpropanoyl)oxy]methyl} hydrogen [2-bromo-4-(3-oxo -2,3-diphenylpropyl) phenyl](difluoro)methylphosphonate;

Example 13: Bis{[(2,2-dimethylpropanoyl)oxy]methyl} [2-bromo-4-(3-oxo-2,3-diphenylpropyl) phenyl] (difluoro)methylphosphonate;

Example 14: 1-{[[[2-bromo-4-(3-oxo-2,3-diphenylpropyl)phenyl](difluoro)methyl] (hydroxy) phosphoryl]oxy}-2-methylpropyl propionate;

Example 15: [1-(isobutyryloxy)ethyl] hydrogen[2-bromo-4-(3-oxo-2,3-diphenylpropyl)phenyl] (difluoro) methylphosphonate;

Example 16: Bis[(isobutyryloxy)methyl] [2-bromo-4-(3-oxo-2,3-diphenylpropyl)phenyl] (difluoro) methylphosphonate;

Example 17: [(isobutyryloxy)methyl] hydrogen [2-bromo-4-(3-oxo-2,3-diphenylpropyl)phenyl] (difluoro)methylphosphonate;

Example 18: Bis{[(isopropoxycarbonyl)oxy]methyl}[2-bromo-4-(3-oxo-2,3-diphenylpropyl) phenyl](difluoro) methylphosphonate;

Example 19: [(isopropoxycarbonyl)oxy]methyl hydrogen [2-bromo-4-(3-oxo-2,3-diphenyl)phenyl] (difluoro) methylphosphate;

Example 20: Dibenzyl[2-bromo-4-(3-oxo-2,3-diphenylpropyl)phenyl](difluoro)methylphosphonate;

Example 21: Benzyl hydrogen [2-bromo-4-(3-oxo-2,3-diphenylpropyl)phenyl](difluoro) methylphosphonate;

Example 22: [2-bromo-4-(3-oxo-2-phenylbutyl)phenyl] (difluoro)methylphosphonic acid;

Example 23: {2-bromo-4-[3-oxo-2-phenyl-3-(1,3-thiazol-2-yl)propyl]phenyl}(difluoro) methylphosphonic acid; and Example 24: {2-bromo-4-[2-(4-methoxy-1,3-thiazol-2-yl)-3-oxo-3-phenylpropyl)phenyl}(difluoro) methylphosphonic acid.

12. A compound as recited in claim 11, wherein one group G is selected from phenyl, —CHR'phenyl and —CHR'OC(=O)R", and the second group G is independently selected from H, phenyl, —CHR'phenyl and —CHR'OC(=O)R", wherein each R' is H or $C_{1-6}$alkyl and each R" is —$C_{1-6}$alkyl, wherein $C_{1-6}$alkyl and —$OC_{1-6}$alkyl in each occurrence is optionally substituted with one or more substituents independently selected from 1–5 halogen atoms, a phenyl group, or a mixture of these, and each phenyl group in each occurrence is optionally substituted with 1–3 substituents independently selected from halogen, —$CH_3$, —$CF_3$, —$OCH_3$ and —$OCF_3$.

13. A compound as recited in claim 11, wherein one substituent group G is H.

14. A compound as recited in claim 11, wherein the two groups G are the same.

15. A pharmaceutical composition which is comprised of a compound in accordance with claim 1 in combination with a pharmaceutically acceptable carrier.

16. A pharmaceutical composition in accordance with claim 15, further comprising a second anti-diabetic or anti-obesity effective compound.

17. A method of treating, controlling or preventing diabetes and complications thereof in a mammalian patient in need of such treatment comprising administering to said patient an anti-diabetic effective amount of a compound in accordance with claim 1.

18. A method of treating, controlling or preventing obesity in a mammalian patient in need of such treatment comprising administering to said patient an anti-obesity effective amount of a compound in accordance with claim 1.

19. A method in accordance with claim 17, further comprising administering to said patient a second anti-diabetic compound or an anti-obesity compound in an amount effective to treat, control or prevent diabetes or obesity.

20. A method in accordance with claim 18, further comprising administering to said patient a second anti-obesity compound or an anti-diabetic compound in an amount effective to treat, control or prevent obesity or diabetes.

21. A pharmaceutical composition in accordance with claim 15, further comprising an HMG-CoA reductase inhibitor.

22. A method in accordance with claim 17, further comprising administering to said patient an effective amount of an HMG-CoA reductase inhibitor.

23. A method for treating, controlling or preventing atherosclerosis in a mammalian patient in need of such treatment comprising administering to said patient an effective amount of a compound of claim 1 and an effective amount of an HMG-CoA reductase inhibitor.

24. A method of treating, preventing, or controlling one or more diseases or conditions selected from the group consisting of Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease, said method comprising the administration of an effective amount of the compound of claim 1.

25. A method of treating, preventing, or controlling one or more diseases or conditions, selected from the group consisting of Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease, said method comprising the administration of an effective amount of the compound of claim 1 and the administration of an effective amount of one or more pharmaceutically active compounds selected from the group consisting of an HMG-CoA reductase inhibitor, an anti-obesity agent, and an antidiabetic compound.

26. A pharmaceutical composition for the treatment, prevention or control of one or more diseases or conditions selected from the group consisting of Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease, said composition comprising an effective amount of a compound of claim 1 and a pharmaceutically acceptable carrier.

27. A pharmaceutical composition for the treatment, prevention or control of one or more diseases or conditions, selected from the group consisting of Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel syndrome, pancreatitis, adipose cell tumors, adipose cell carcinoma, liposarcoma, dyslipidemia, cancer, and neurodegenerative disease, said composition comprising (1) an effective amount of the compound of claim 1, (2) an effective amount of one or more pharmaceutically active compounds selected from the group consisting of an HMG-CoA reductase inhibitor, an anti-obesity agent, and an anti-diabetic agent, and (3) a pharmaceutically acceptable carrier.

28. A pharmaceutical composition for the treatment, prevention or control of one or more diseases or conditions, selected from the group consisting of Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease, said composition comprising:

(1) an effective amount of the compound of claim 1,
(2) an effective amount of one or pharmaceutically active compounds selected from the group consisting of:

(a) insulin sensitizers including (i) PPARγ agonists such as the glitazones (e.g. troglitazone, pioglitazone, englitazone, MCC-555, rosiglitazone, and the like), and compounds disclosed in WO97/27857, 97/28115, 97/28137 and 97/27847; (ii) biguanides such as metformin and phenformin;
(b) insulin or insulin mimetics;
(c) sulfonylureas such as tolbutamide and glipizide, or related materials;
(d) α-glucosidase inhibitors (such as acarbose);
(e) cholesterol lowering agents such as (i) HMG-CoA reductase inhibitors (lovastatin, simvastatin and pravastatin, fluvastatin, atorvastatin, rivastatin and other statins), (ii) sequestrants (cholestyramine, colestipol and a dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and benzafibrate), (v) inhibitors of cholesterol absorption for example beta-sitosterol and (acyl CoA:cholesterol acyltransferase) inhibitors for example melinamide and (vi) probucol;
(f) PPARα/γ agonists;
(g) antiobesity compounds such as appetite suppressants, fenfluramine, dexfenfluramine, phentiramine, sulbitramine, orlistat, neuropeptide Y5 inhibitors (NP Y5 receptor antagonosts), leptin, which is a peptidic hormone, $β_3$ adrenergic receptor agonists, and PPARγ antagonists and partial agonists;
(h) ileal bile acid transporter inhibitors; and
(i) insulin receptor activators; and
(3) a pharmaceutically acceptable carrier.

29. A compound having formula Ia, or a pharmaceutically acceptable salt thereof,

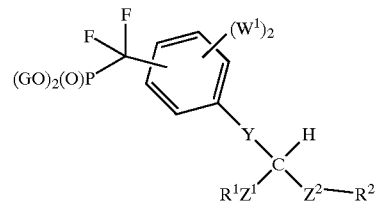

Ia wherein one group —OG is optionally—OH, and wherein one or both groups —OG are groups that are converted to —OH under physiological conditions during or after administration to a mammalian patient, thereby yielding a phosphonic acid group, or a salt thereof, $R^1$ and $R^2$ are each independently selected from Aryl($R^a$)$_{0-3}$ and Het($R^a$)$_{0-3}$;

wherein, each $R^a$ independently represents a member selected from the group consisting of: Aryl, OH, CN, halogen, $CO_2H$, $CO_2C_{1-6}$alkyl, $OC_{1-6}$alkyl, $C_{1-6}$alkyl, $OC_{1-10}$alkyleneCO$_2$H, OAryl, $C_{0-6}$alkyleneSO$_3$H, $C_{0-6}$alkyleneCO$_2$H, $C_{0-6}$alkyleneCO$_2C_{1-6}$alkyl, $C_{0-6}$alkyleneCO$_2C_{2-6}$alkenyl, $C_{0-6}$alkyleneC(O)$C_{1-6}$alkyl, C(O)NR$_3$·R$_{4'}$, $_{NR3}$·R$_{4'}$, $_{C1-6}$haloalkyl, $OC_{1-6}$haloalkyl, S(O)$_y$C$_{1-6}$alkyl, S(O)$_y$NR$^{3'}$R$^{4'}$, and Het, wherein y is 0, 1, or 2, wherein Het, Aryl, alkyl, and alkenyl in $R^a$ are optionally substituted with 1–3 substituents independently selected from halogen, $C_{1-6}$alkyl, $C_{1-6}$haloalkyl, $CO_2H$, $CO_2C_{1-6}$alkyl, $OC_{1-10}$alkyl, OH, Het and Aryl, where said Het and Aryl are optionally substituted with 1–2 substituents independently selected from halogen, $C_{1-3}$alkyl, $OC_{1-3}$alkyl, $CF_3$, and $OCF_3$;

Aryl is a 6–14 membered carbocyclic aromatic ring system comprising 1–3 phenyl rings, wherein said rings are fused together so that adjacent rings share a common side when there is more than one aromatic ring;

Het represents a 5–10 membered aromatic ring system comprising one ring or two fused rings, 1–4 heteroatoms, 0–4 of which are N atoms and 0–2 of which are O or $S(O)_y$ wherein y is 0–2, and 0–2 carbonyl groups;

y, $Z^1$ and $Z^2$ each independently represents —$(CR^3R^4)_a$—X—$(CR^3R^4)_b$—wherein a and b are either 0 or 1, such that the sum of a and b equals 0, 1 or 2;

X represents a bond, O, $S(O)_y$, $NR^{3'}$, C(O), OC(O), C(O)O, C(O)$NR^{3'}$, $NR^{3'}$C(O) or —CH=CH—, where y is as previously defined;

$R^3$ and $R^4$ are independently H, halo, $C_{1-3}$alkyl, or $C_{1-3}$haloalkyl;

each $R^{3'}$ is independently selected from the group consisting of: H, $C_{1-6}$alkyl, $C_{1-6}$haloalkyl, OH, C(O)$C_{1-6}$alkyl, C(O)Aryl, C(O)Het, C(O)$C_{1-6}$haloalkyl, Aryl and Het;

each $R^{4'}$ is independently selected from the group consisting of: H, $C_{1-6}$alkyl, $C_{1-6}$haloalkyl, Aryl and Het; and each $W^1$ is independently selected from the group consisting of: H, OH, CN, halogen, $OC_{1-6}$alkyl$(R^a)_{0-3}$, $S(O)_yC_{1-6}$alkyl$(R^a)_{0-3}$, with y equal to 0–2, $S(O)_3H$, $C_{1-6}$alkyl$(R^a)_{0-3}$, $C_{1-6}$haloalkyl$(R^a)_{0-3}$, $CO_2H$, $CO_2C_{1-6}$alkyl$(R0-2, a)_{0-3}$, $CO_2C_{1-6}$haloalkyl$(R^a)_{0-3}$, $CO_2C_{2-6}$alkenyl$(R^a)_{0-3}$, $C(O)C_{1-6}$alkyl$(R^a)_{0-3}$, $C(O)NR^{3'}R^{4'}$, $S(O)_yNR^{3'}R^{4'}$, $NR^{3'}R^{4'}$, Aryl and Het, wherein $R^{3'}$ and $R^{4'}$ are as defined above, and wherein Aryl and Het may be unsubstituted or are optionally substituted with 1–3 substituents independently selected from the group consisting of halogen, $C_{1-6}$alkyl, $C_{1-6}$haloalkyl, $CO_2H$, $CO_2C_{1-6}$alkyl, $OC_{1-6}$alkyl, $OC_{1-6}$haloalkyl, and OH; or the two $W^1$ groups are on adjacent positions of the aromatic ring and are taken in combination to represent a fused phenyl ring.

* * * * *